US008685638B2

(12) United States Patent
Bhatia et al.

(10) Patent No.: US 8,685,638 B2
(45) Date of Patent: Apr. 1, 2014

(54) CELLULAR MICROARRAYS FOR SCREENING DIFFERENTIATION FACTORS

(75) Inventors: Sangeeta N. Bhatia, Lexington, MA (US); Christopher Flaim, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 318 days.

(21) Appl. No.: 11/336,131

(22) Filed: Jan. 19, 2006

(65) Prior Publication Data

US 2006/0160066 A1 Jul. 20, 2006

Related U.S. Application Data

(60) Provisional application No. 60/645,556, filed on Jan. 20, 2005.

(51) Int. Cl.
| | | |
|---|---|---|
| *C12Q 1/00* | (2006.01) | |
| *C12M 1/34* | (2006.01) | |
| *C12Q 1/02* | (2006.01) | |
| *C12Q 1/18* | (2006.01) | |
| *C12N 5/00* | (2006.01) | |
| *C12N 5/02* | (2006.01) | |
| *C12N 5/04* | (2006.01) | |
| *C12Q 1/04* | (2006.01) | |
| *C12Q 1/20* | (2006.01) | |
| *C12N 5/07* | (2010.01) | |

(52) U.S. Cl.
USPC ............... 435/4; 435/29; 435/32; 435/325; 435/397; 435/404

(58) Field of Classification Search
None
See application file for complete search history.

(56) References Cited

U.S. PATENT DOCUMENTS

| | | | |
|---|---|---|---|
| 4,107,121 A | 8/1978 | Stoy | |
| 4,663,358 A | 5/1987 | Hyon et al. | |
| 4,943,618 A | 7/1990 | Stoy et al. | |
| 5,252,692 A | 10/1993 | Lovy et al. | |
| 5,688,855 A | 11/1997 | Stoy et al. | |
| 5,744,305 A | 4/1998 | Fodor et al. | |
| 6,296,702 B1 | 10/2001 | Bryning et al. | |
| 6,440,217 B2 | 8/2002 | Vann et al. | |
| 6,479,299 B1 | 11/2002 | Parce et al. | |
| 6,579,367 B2 | 6/2003 | Vann et al. | |
| 6,746,104 B2 * | 6/2004 | Ellson et al. | 506/30 |
| 6,849,127 B2 | 2/2005 | Vann et al. | |
| 7,288,405 B2 | 10/2007 | Shuler et al. | |
| 2001/0053897 A1 * | 12/2001 | Frate et al. | 604/304 |
| 2003/0082795 A1 | 5/2003 | Shuler et al. | 435/286.1 |
| 2004/0152067 A1 * | 8/2004 | Wang et al. | 435/4 |
| 2005/0009204 A1 | 1/2005 | Fang et al. | 436/518 |
| 2006/0173394 A1 * | 8/2006 | Stroock et al. | 602/41 |

FOREIGN PATENT DOCUMENTS

WO  WO 91/07087  5/1991

OTHER PUBLICATIONS

Oh et al.1981 Deposition of plasma fibronectin in tissues. Proceedings of National Academy of Sciences of the USA, vol. 78, No. 5, pp. 3218-3221.*
Polte et al. Mar. 2004. Extracellular matrix controls myosin light chain phosphorylation and cell contractility through modulation of cell shape and cytoskeletal prestress. American J. Physiol. Cell Physiology, vol. 286, pp. C518-C528.*
Tang et al. 2003. Molding of Three-Dimensional Microstructures of Gels. Journal of American Chemical Society, vol. 125, pp. 12988-12989.*
International Search Report, International Application No. PCT/US06/01893 dated Jul. 29, 2008.
Liu et al., "Engineering protein and cell adhesivity using PEO-terminated triblock polymers", J Biomed Mater Res 60: pp. 126-134, 2002.
Cooley, P. et al., "Applications of Ink-Jet Printing Technology to BioMEMS and Microfluidic Systems," *Journal of the Association for Laboratory Automation*, 200210 US vol. 7, No. 5, Oct. 2002.
Okorie, U. M. et al., "Matrix Protein Microarrays for Spatially and Compositionally Controlled Microspot Thrombosis Under Laminar Flow," *Biophysical Journal Biophys. Soc*, USA vol. 91 No. 9 pp. 33-39, Nov. 2006.
International Search Report for EP 06718897, mailed on Oct. 27, 2009, 2 pp.
Australian Office Action for Application No. 2006206426, dated Jun. 7, 2010.
Chen, Christopher S. et al., "Geometric Control of Cell Life and Death," Science, vol. 276:1425-1428 (1997).
Chen, Christopher S. et al., "Using Self-Assembled Monolayers to Pattern ECM Proteins and Cells on Substrates," Methods in Molecular Biology, vol. 139:209-219 (2000).
Pelham, Robert J. et al., "Cell locomotion and focal adhesions are regulated by substrate flexibility," Proc. Natl. Acad. Sci. USA; vol. 94:13661-13665 (1997).
Wang, Ning et al., "Mechanical behavior in living cells consistent with the tensegrity model," PNAS, vol. 98 (14):7765-7770 (2001).
Ito, Y. et al., (2003), "Preparation of a protein micro-array using a photo-reactive polymer for a cell-adhesion assay," *Biomaterials* 24(18):3021-3026.

(Continued)

*Primary Examiner* — Jon P Weber
*Assistant Examiner* — Kailash C Srivastava
(74) *Attorney, Agent, or Firm* — Nelson Mullins Riley & Scarborough LLP; Debra J. Milasincic, Esq.

(57) ABSTRACT

Provided is a microarray platform for the culture of cells atop combinatorial matrix mixtures; enabling the study of differentiation in response to a multitude of microenvironments in parallel.

28 Claims, 10 Drawing Sheets

(56) References Cited

OTHER PUBLICATIONS

Jeon, N.L. et al. (2000), "Generation of Solution and surface gradients using microfluidic systems," *Langmuir* 16(22):8311-8316.

Kane, R.S. et al. (1999), "Patterning proteins and cells using soft lithography," *Biomaterials* 20(23-24):2363-76.

Larson et al. (1987), "Junctional transfer of small molecules in cultured bovine brain microvascular endothelial cells and pericytes," *Microvasc. Res.* 34:184.

McGrath et al. (1991), "Cytometrically coherent transfer of receptor proteins on microporous membranes," *BioTechniques* 11:352-361.

Moloney et al. (2002), "Immobilisation of semliki forest virus for alomic force microscopy," *Ultramicroscopy* 99:275-279.

Norton, L.W. (2005), "In vitro characterization of vascular endothelial growth factor and dexamethasone releasing hydrogels for implantable probe coatings," *Biomaterials* 26(16):3285-3297.

Park, T.H. et al. (2003), "Integration of cell culture and microfabrication technology," *Biotechnol Prog* 19(2):243-53.

Revzin, A. et al. (2004), "Designing a hepatocellular microevironment with protein microaaraying and poly(ethylene glycol) photolithography," Langmuir 20:2999-3005.

Ruoff and Hay (1979), "Metabolic and temporal studies on pancreatic exocrine cells in culture," *Cell Tissue Res.* 204:243-252.

Seglen, P.O. (1976), "Preparation of isolated rat liver cells," In *Methods in Cell Biology*, Academic Press, New York, vol. 13, pp. 29-83.

Watt, A. J. et al. (2001), "A gene trap integration provides an early in situ marker for hepatic specification of the foregut endoderm," *Mech. Dev.* 100:205-215.

Ziauddin, J. et al. (2001), "Microarrays of cells expressing defined cDNAs," *Nature* 411(6833):107-10.

Bhatia, Sangeeta N. et al., "Controlling cell interactions by micropatterning in co-cultures: Hepatocytes and 3T3 fibroblasts," Journal of Biomedical Materials Research, vol. 34:180-199 (1997).

Clemence, Jean-Francois et al., "Photoimmobilization of a Bioactive Laminin Fragment and Pattern-Guided Selective Neuronal Cell Attachment" Bioconjugate Chem., vol. 6:411-417 (1995).

Lom, Barbara et al., "A versatile technique for patterning biomolecules onto glass coverslips," Journal of Neuroscience Methods, vol. 50:365-397 (1993).

Canadian Office Action for Application No. 2,601,918, 2 pages, dated May 14, 2012.

European Office Action for Application No. 06718897.9, 7 pages, dated Nov. 28, 2011.

Nelson, Celeste M. et al., "Degradation of Micropatterned Surfaces by Cell-Dependent and -Independent Processes," Langmuir, vol. 19:1493-1499 (2003).

Canadian Office Action for Application No. 2,601,918, 3 pages, dated Jul. 4, 2013.

Anderson, D.G. (2004). "Nanoliter-scale synthesis of arrayed biomaterials and application to human embryonic stem cells," *Nat. Biotechnol* 22:863-866.

Berry and Friend (1969). "High-yield preparation of isolated rat liver parenchymal cells," *J. Cell Biol.* 43:506-520.

Dunn, J.C. (1989). "Hepatocyte function and extracellular matrix geometry: long-term culture in a sandwich configuration," *FASEB J.* 3:174-177.

Falsey, J.R. et al. (2001). "Peptide and small molecule microarray for high throughput cell adhesion and functional assays," *Bioconjugate Chemistry* 12(3):346-353.

Flaim, C. et al. (2005). "An extracellular matrix microarray for probing cellular differentiation," *Nature Methods* 2(2):119-125.

Folch, A. et al. (1999). "Molding of deep polydimethylsiloxane microstructures for microfluidics and biological applications," *Journal of Biomechanical Engineering-Transactions of the ASME* 121(1):28-34.

Forrester, L.M. et al. (1996). "An induction gene trap screen in embryonic stem cells: Identification of genes that respond to retinoic acid in vitro," *Proc. Natl. Acad. Sci. U.S.A.* 93:1677-1682.

Freshney (1987). "Culture of Animal Cells," In *A Manual of Basic Technique*, 2nd Ed., A.R. Liss, Inc., New York. Ch. 9, pp. 107-126, and Ch. 11 and 12, pp. 137-168.

Hansen, C.L. et al. (2002). "A robust and scalable microfluidic metering method that allows protein crystal growth by free interface diffusion," *PNAS* 99(26):16531-16536.

Hay (1979). "Methodological Surveys in Biochemistry," vol. 8 In *Cell Populations*. London, Ellis Hornwood, Ltd., pp. 143-160.

* cited by examiner

CELLULAR MICROARRAYS FOR SCREENING DIFFERENTIATION FACTORS

CROSS-REFERENCE TO RELATED APPLICATIONS

This application claims priority under 35 U.S.C. §119 to U.S. Provisional Application Ser. No. 60/645,556, filed Jan. 20, 2005, the disclosure of which is incorporated herein by reference.

STATEMENT REGARDING FEDERAL SPONSORED RESEARCH

The U.S. Government has certain rights in this invention pursuant to Grant No. DK56966 and DK65152 awarded by the National Institutes of Health (NIH).

FIELD OF THE INVENTION

The invention is directed to cell culture techniques and systems and more particularly to cellular microarrays for screening factors that modulate cell differentiation, growth, survival, and/or activity.

BACKGROUND

Microenvironments play a role in modulating cell growth, differentiation and activity. However, current in vitro environments used to culture cells fail to provide optimal microenvironments to simulate in vivo cell/tissue growth and differentiation. Cell culture techniques and the understanding of the complex interactions cells have with one another and the surrounding environment have improved in the past decade. There is now a better understanding of the role extracellular matrix materials play in the proliferation and development of artificial tissues in vitro. Historically cell culture techniques and tissue development fail to take into account the necessary microenvironment for cell-cell and cell-matrix communication as well as an adequate diffusional environment for delivery of nutrients and removal of waste products.

While many methods and bioreactors have been developed to grow tissue masses for the purposes of generating artificial tissues for transplantation or for toxicology studies, these bioreactors do not adequately simulate in vitro the mechanisms by which nutrients and gases are delivered to tissue cells in vivo.

SUMMARY OF THE INVENTION

The invention provides a cell culture substrate, comprising a plurality of microspot islands or microwells in an array, wherein the microspot islands or microwells comprise an insoluble factor or an insoluble and soluble factor, wherein the insoluble factor promotes cellular adhesion. In one aspect, the cell culture substrate comprises a polymerized biopolymer such as a hydrogel. In another aspect, the insoluble factor is an extracellular matrix protein. The culture substrate may further comprising a plurality of microfluidic channels connecting one or more microspot islands or microwells to a fluid flow.

The invention also provides a method of making a microarray. The method comprises spotting a plurality of locations on a substrate with an adherence material. In one aspect, the adherence material is an extracellular matrix protein. The substrate may be layered with a hydrogel. The hydrogel may be etched at each of the plurality of locations to form a microwell.

The culture substrates of the invention are useful for culturing one or more cell types that adhere to each location comprising an insoluble and/or soluble material (e.g., an adherence material).

The invention also provides a method of making a culture substrate, comprising spotting a material on the substrate using a device capable of spotting from about 1 to about 1000 nanoliters of material to generate an island of material.

The invention also provides a microarray formed by the methods and processes of the invention. A culture system is also provided by the invention.

The invention provides an assay system useful for protein production, clone amplification and selection, and/or screening of compounds (e.g. soluble and insoluble) useful for cell type maturation, growth and differentiation. The assay system comprises contacting a microarray of the invention with one or more cell-types and measuring an activity selected from gene expression, cell function, metabolic activity, morphology, and a combination thereof.

Other aspects of the invention will be understood from the drawings, the detailed description, and examples provided below.

DETAILED DESCRIPTION

Figure 1:
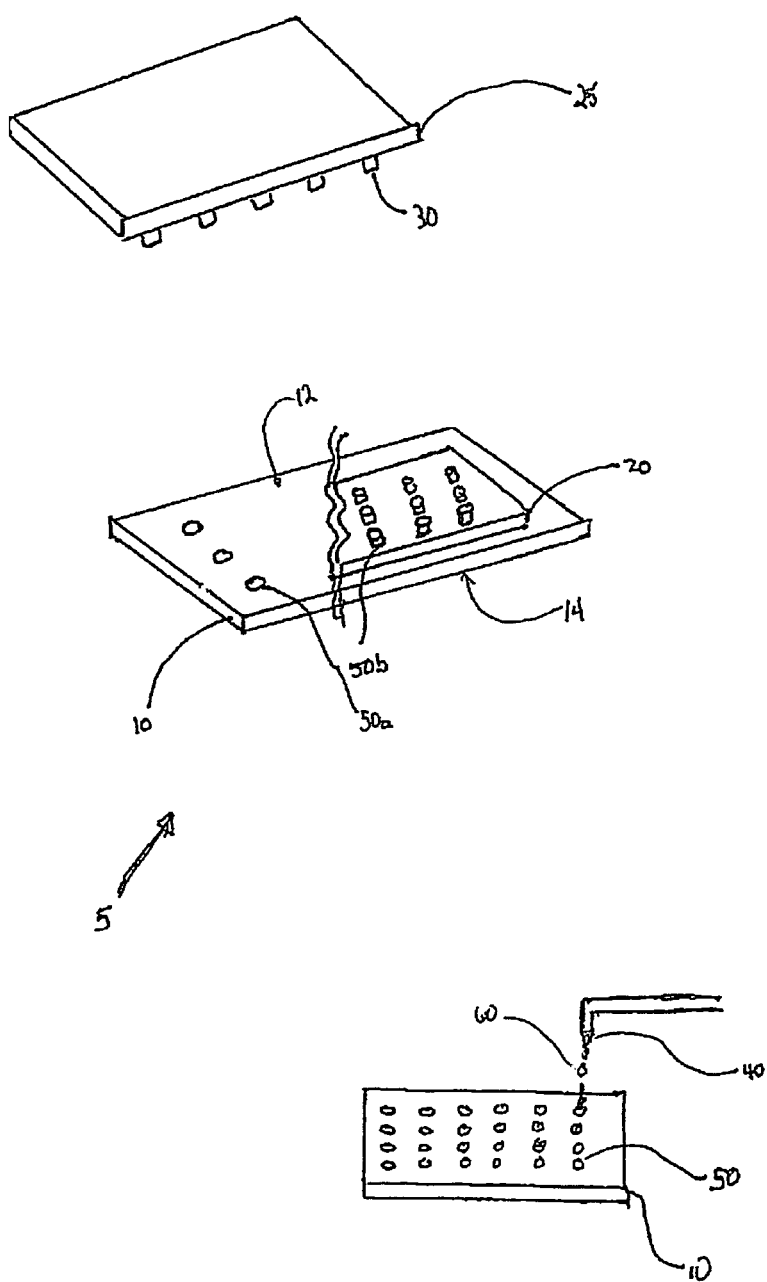
FIG. 1 is a schematic depicting a microarray of the invention.

As used herein and in the appended claims, the singular forms "a," "and," and "the" include plural referents unless the context clearly dictates otherwise. Thus, for example, reference to "a microwell" includes a plurality of such microwells and reference to "the cell" includes reference to one or more cells known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

The diversity of biological niches mandates a systematic approach to investigating optimal cell culture environments. Miniaturized arrays of living cells, like DNA microarrays, offer the potential of a more global picture of the role of soluble and insoluble cues on cell fate and function.

The cellular microenvironment plays a critical role in determining cell fate and function. Extracellular determinants of survival, proliferation, migration, and differentiation include soluble signals (cytokines, dissolved gasses), insoluble cues (extracellular matrix, cell-cell interactions, biomaterials), and physical stimuli (shear stress). Miniaturization of bioassays using multiwell plates and robotic liquid handling enables combinatorial screening of the effects of soluble species on cellular behavior; however, analogous approaches for screening the effects of insoluble cues are in their infancy. Cellular interactions with the extracellular matrix (ECM) are of particular interest as ligation of an integrin can directly induce cellular signaling, modulate the response to other agonists, and influence the behavior of other integrins, a phenomenon called crosstalk. Thus, the extracellular matrix plays a role in developing an integrated picture of the microenvironment in the fate of many diverse cell types.

Cell-ECM interactions have been studied using several approaches. Typically, purified matrix proteins are adsorbed to cell culture substrates alone or in a combination requiring on the order of 10 µg of protein per 96-well plate; however, purified matrix for a combinatorial screen can be prohibitively expensive and/or simply unavailable in sufficient quantity. These '2-dimensional' approaches are complemented by so-called '3-dimensional' approaches such as embedding cells within ECM gels. More complex ECM has also been investigated using cell-derived matrix in vitro or decellularized tissue sections. In addition to natural ECM components, biomaterial approaches have yielded several hybrid matrices with tethered biomolecules and tunable degradation in a 3-dimensional hydrogel context. Studies of the interaction of cell-ECM provides a critical first step towards developing a comprehensive understanding of insoluble cues in the cellular microenvironment.

Figure 2:
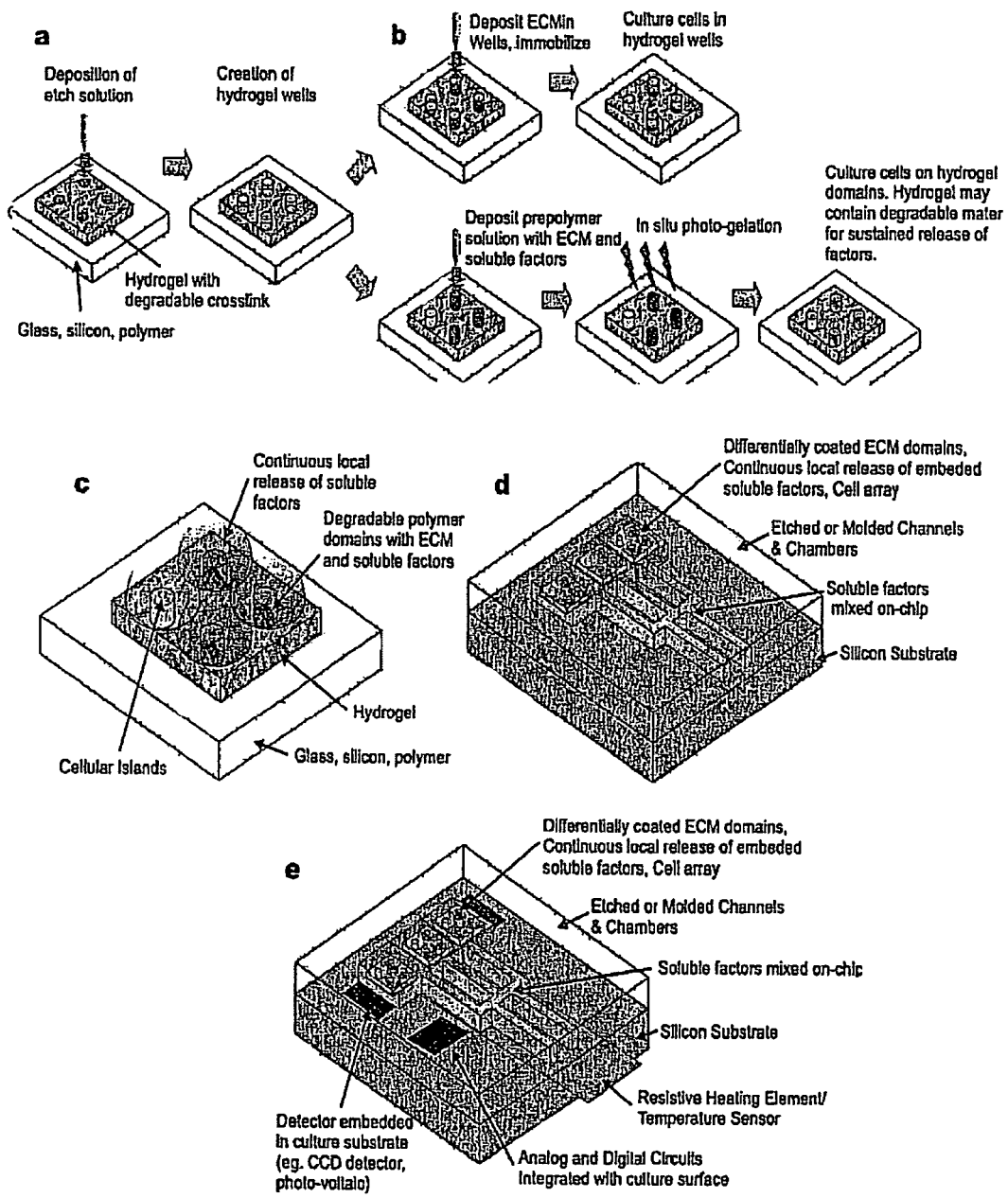
FIG. 2A-F is a schematic depiction of fabrication and use of a microarray of the invention. Integration of wells, sustained release, microfluidics and electronic sensors and actuators can be included in the methods and systems. (A) Shows the creation of hydrogel wells by spotting periodic acid etch solution on acrylamide gel with N,N'-(1,2-Dihydroxyethylene)bisacrylamide (DHEBA) cross-linker. (B) Shows two examples for potential use: spotting and immobilizing proteins to bottom of wells, and spotting and gelation of prepolymer solution containing Extracellular Matrix (ECM) materials and soluble factors for continuous local release. (C) Illustration of sustained release mode of use. Hydrogel wells have been filled with degradable matrix that releases soluble factors locally. (D) Overlaying with microfluidic channels for mixing soluble factors and delivery to culture chambers. (E) Integration of electronic components, such as heating, digital processing, analog processing, and sensors. (F) A schematic demonstrating a top and side view of microfluidic delivery and parallel screening techniques.
Figure 2F:
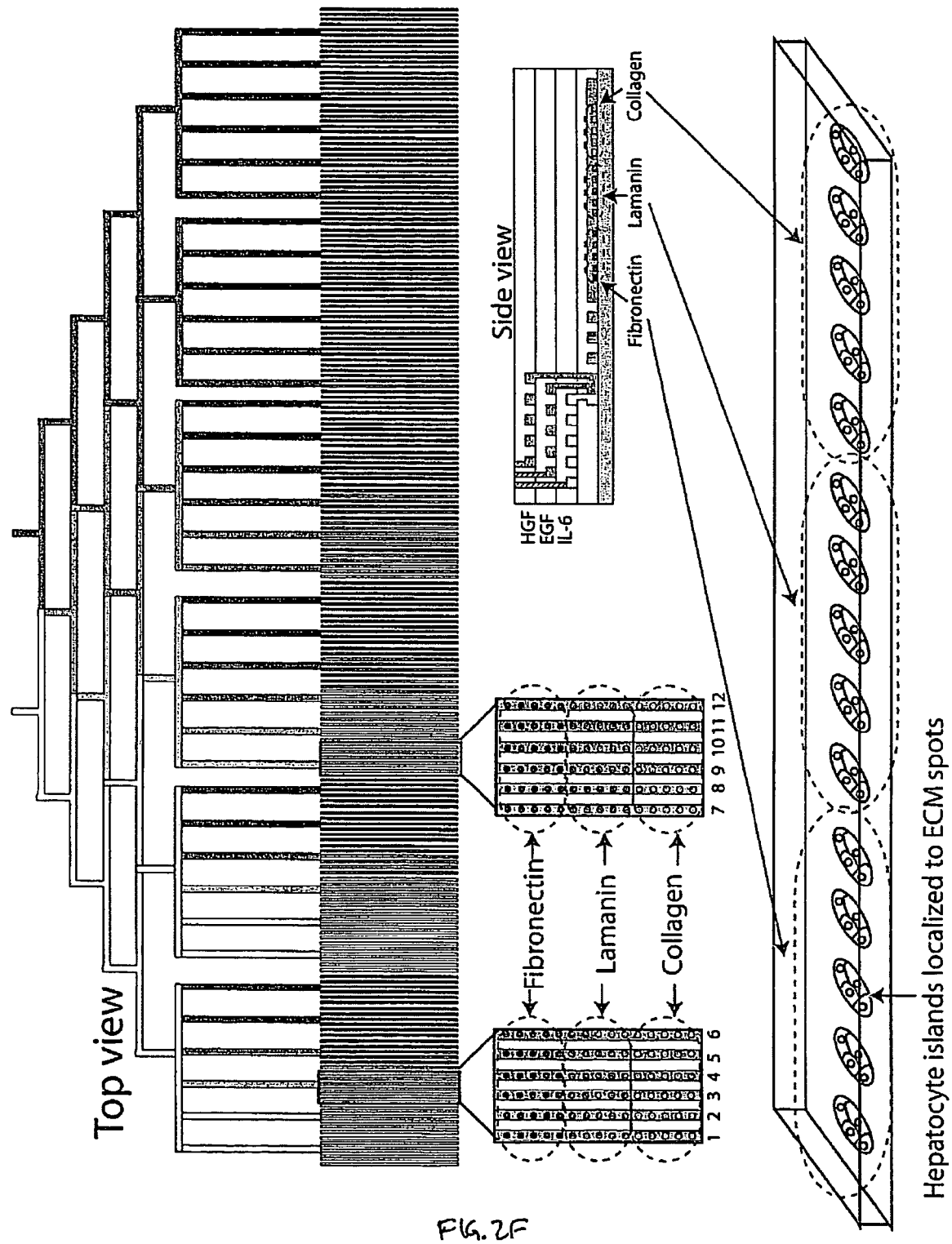

Growth factor signals synergistically interact in permissive ECM microenvironments. Cross talk between ECM proteins and soluble factors would be best investigated using a highly parallel microfluidic platform integrating robotic spotting of substrates with a microfluidic network generating combinatorial soluble factor mixtures. Such a platform can be used in other experiments to investigate other cellular pathways involving multiple soluble factor interactions and integrin cross talk. Microfluidics allows for on-chip serial dilution of soluble factors through the exploitation of laminar flow inside the microchannels as shown in FIG. 2D-F. In addition, these dilutions can be performed on multiple soluble factors and combined on-chip before delivery to discreet microdomains of ECM proteins to study the combined effect of soluble and insoluble factors on cell fate and function. A schematic of this is shown in FIG. 2.

The invention provides a robust method to create cell arrays using a spotter device (e.g., a DNA spotter device) and off-the-shelf chemicals. Culturing parenchymal cells (e.g., primary hepatocytes), ES cells, and/or stromal cells on combinatorial mixtures of extracellular matrix (ECM) in the methods and systems of the invention yields novel insights into the role of the microenvironment using 1000 times less protein than conventional methods. The methods and systems of the invention are amenable to depositing almost any insoluble or soluble material/biological material, such as polysaccharides, proteoglycans, glycosaminoglycans, membrane bound proteins, DNA, siRNA, and tethered growth factors or peptide signaling motifs. The methods and systems can also be easily adapted to: exploit lineage-specific fluorescent reporter strategies, co-cultivation of epithelia and stroma, and/or combinations of soluble factors to screen the effects of growth factors or small molecules in conjunction with underlying matrix.

Referring to FIG. 1, there is shown a microarray 5 of the invention. Microarray 5 comprises a biologically compatible culture substrate 10 having a first surface 12 and a second surface 14. The substrate 10 can comprise a plurality of spots 50a or microwells 50b. Alternatively, the substrate 10 can be layered with a gel pad 20. Gel pad 20 may be fabricated by polymerization of the gel using a template surface plate 25 comprising protuberances 30 such that upon polymerization and removal of the surface plate 25 microwells 50 are formed in the gel pad 20. In another aspect, the gel pad 20 is polymerized and microwells 50 are formed using an etching technique, as described herein. Microwells 50 can be any appropriate size but are typically about 100-200 µm in diameter. A spotter device 40 can be used to deliver the etching material. In addition, spotter device 40 can be used to deliver soluble or insoluble biological material 60 to microwells 50.

Various culture substrates 10 can be used in the methods and systems of the invention. Such substrates include, but are not limited to, glass, polystyrene, polypropylene, stainless steel, silicon and the like. The choice of the microarray surface should be taken in to account where spatially separated cellular islands are to be maintained.

The cell culture surface (e.g., the first surface 12) can be chosen from any number of rigid or elastic supports. For example, cell culture material can comprise glass or polymer microscope slides that have a plurality of relatively larger culture domains delineated by hydrophobic ink, silicone well dividers, 3D surface topography, or a combination of these. Protein spots can thus be deposited, and cells cultured in each culture well in a manner similar to that described herein.

The cell culture surface/substrate used in the methods and systems of the invention can be made of any material suitable for culturing mammalian cells. For example, the substrate can be a material that can be easily sterilized such as plastic or other artificial polymer material, so long as the material is biocompatible. Substrate can be any material that allows cells and/or tissue to adhere (or can be modified to allow cells and/or tissue to adhere or not adhere at select locations) and that allows cells and/or tissue to grow in one or more layers. Any number of materials can be used to form the substrate/surface, including, but not limited to, polyamides; polyesters; polystyrene; polypropylene; polyacrylates; polyvinyl compounds (e.g. polyvinylchloride); polycarbonate (PVC); polytetrafluoroethylene (PTFE); nitrocellulose; cotton; polyglycolic acid (PGA); cellulose; dextran; gelatin, glass, fluoropolymers, fluorinated ethylene propylene, polyvinylidene, polydimethylsiloxane, polystyrene, and silicon substrates (such as fused silica, polysilicon, or single silicon crystals), and the like. Also metals (gold, silver, titanium films) can be used.

When certain materials such as nylon, polystyrene and similar materials are used as the substrate it is advisable to pre-treat the substrate prior to inoculation with cells in order to enhance the attachment of cells to the substrate. For example, prior to inoculation with stromal cells and/or parenchymal cells, nylon substrates should be treated with 0.1M acetic acid, and incubated in polylysine, FBS, and/or collagen to coat the nylon. Polystyrene could be similarly treated using sulfuric acid.

Additionally, rigid surfaces modified with a hydrogel can also be used. In one embodiment, user defined ECM protein mixtures are deposited on a hydrogel modified surface that is otherwise non-adhesive for cells. The surface may be a modified surface including, for example, a surface that has been modified or coated with a gel pad 20. For example, in one aspect of the invention, a substrate 10 is coated with polyacrylamide gel such that the surface allows ECM materials to be stored locally in a hydrated microwell environment, yet resists adsorption of serum proteins. The non-fouling nature of acrylamide prevents cell migration over relatively long periods of time (~28 days) in comparison to other cell patterning techniques (~7 days) which use agarose, pluronics, serum albumin, or polyethylene glycol. Dehydrated polyacrylamide substrates are thought to swell during spotting and retain proteins through hydrophobic interactions. In order to maintain attachment of the gel material to a substrate surface, the surface (e.g., glass) can be densely hydroxylated prior to silanization, a highly porous glass substrate, or alternate silane coupling agents.

Alternatively, the hydrogel can be modified such that cell attachment is inhibited for a short period of time. During this period, a first cell type can be attached to the protein spotted domains. A second cell type can then be introduced, which can attach to regions surrounding the first cell type. As a further embodiment, the invention provides for the creation of polymer hydrogel "wells" by using a spotter device to deposit an etching solution (such as a mild periodic acid solution) to a hydrogel surface containing a degradable component. These etched wells can then be further modified individually by subsequently depositing protein solutions or pre-polymer solutions (with or without proteins) to the well locations using the DNA-spotter. Proteins or pre-polymer solutions can thus be immobilized using photo-gelation or chemical crosslinking. Additionally, degradable polymer matrices can be incorporated into the hydrogel substrate that would allow for local sustained release of soluble factors. Again, each well can be tailored individually using the above mentioned techniques.

Polymeric hydrogels and gel pads can be used in the methods and systems of the invention to facilitate cellular attachment and localization (e.g., by forming microwells). In one aspect, microwells are formed in a gel layer/pad on a substrate to retain biological molecules including, but not limited to, proteins, peptides, oligonucleotides, polynucleotides, polysaccharides, lipids and other biological molecules.

Deformable hydrogel can be used in the methods and systems of the invention. Deformable hydrogels include polyacrylamide hydrogels. In some embodiment, the hydrogel will comprise components that weakly repulse cells, thereby providing low background binding. In one embodiment, the substrate comprises a polymerized mixture including acrylamide and hydrophilic acrylates.

Typically hydrogels are selected such that specific binding to desired spots or wells by the cells is promoted and non-specific binding is reduced. Those of skill in the art will understand that cells vary in their ability to adhere to a substrate.

Hydrogels provide for hydration of bound cells, lack of diffusion of insoluble materials, low background binding of cells and free flow of cells across the surface of the microarray due to weak cell repulsion.

The cell culture surface can be created on a deformable membrane which allows for the cells to be actively stretched during culture. The membrane can be composed of an elastomeric material (such as PDMS), hydrogel, or other such material. Membrane deformation can be controlled using any of a multitude of suitable methods. These include MEMS motors incorporated into the culture chip, and connected to the culture substrate and electroactive polymers that respond to electric field by undergoing a shape change. Examples of such materials include electrostrictive materials such as thin acrylate films with deformable electrodes placed on both sides of the material. An applied electric field causes the acrylate film to compress or expand, resulting in a concurrent change in surface area such that the total volume of the film remains constant. Such materials are know as "electrostrictive" in the field of electroactive polymers. Methods for generating force and deformation in a pliable material using electric fields ("electrophoretic"), or alternating non-uniform electric fields ("dielectrophoretic") are also possible by using a material that is responsive to such modes of excitation. As an example, the gel material may incorporate charged particles, or neutral particles that can experience an induced dipole force in the presence of a uniform or non-uniform electric field. The electric field can be generated by placing the gel material on an electrode array, which can apply a static electric field, or an alternating electric field of the appropriate frequency to induce a net force on the dielectric medium of the gel.

By deformable is meant that a deformable material is capable of being damaged by contact with a rigid instrument. Examples of deformable materials include hydrogels, polyacrylamide, nylon, nitrocellulose, polypropylene, polyester films, such as polyethylene terephthalate, and the like. Non-deformable materials include materials that do not readily bend, and include glass, fused silica, nanowires, quartz, plastics, e.g. polytetrafluoroethylene, polypropylene, polystyrene, polycarbonate, and blends thereof, and the like; metals, e.g. gold, platinum, silver, and the like. In some aspect, a deformable material may be layered upon a non-deformable material.

Another example of hydrogels useful in the methods and systems of the invention include polyvinylalcohol (PVA), physically cross-linked by partial crystallization of the chain. Such hydrogels are described, for example, in U.S. Pat. No. 4,663,358. Another example are hydrogels based on segmented polyurethanes or polyureas, an example of which is described in U.S. Pat. No. 5,688,855. In principle, polypeptide or polysaccharide hydrogels could be used, an example of which is agarose or cross-linked hyaluronic acid. Other hydrogels include partially hydrolyzed or aminolyzed polyacrylonitrile (PAN), an example of which is described in U.S. Pat. Nos. 4,943,618; 4,107,121, and 5,252,692. Typically, substrates and hydrogels used in the invention are sufficient biocompatible and do not release any harmful substances.

The gel layer/pad can be conveniently produced as thin sheets on a solid substrate (e.g., a glass slide, cell culture plate, and the like), typically by depositing a solution of acrylamide monomer, a crosslinker such methylene bisacrylamide, and a catalyst such as N,N,N',N'-tetramethylethylendiamine (TEMED) and an initiator such as ammonium persulfate for chemical polymerization, or 2,2-dimethoxy-2-phenyl-acetophone (DMPAP) for photo-polymerization. In one aspect, the gel layer/pad is formed between two glass surfaces (e.g., glass plates or microscope slides) using a spacer to obtain the desired thickness of the polymeric gel. Generally, the acrylamide monomer and crosslinker are prepared in one solution of about 4-5% acrylamide (having an acrylamide/bisacrylamide ratio of 19/1) in water/glycerol, with a nominal amount of initiator added. The solution is polymerized and crosslinked either by ultraviolet (UV) radiation (e.g., 254 nm for at about 15 minutes, or other appropriate UV conditions), or by thermal initiation at elevated temperature (e.g., typically at about 40° C.). Following polymerization and crosslinking, the top glass slide is removed from the surface to uncover the gel. The porosity of the gel is controlled by changing the amount of crosslinker and the percent solids in the monomer solution.

In the fabrication of polyacrylamide gels polymeric hydrogel arrays of the invention (i.e., patterned gels), the acrylamide solution typically is imaged through a mask during the UV polymerization/crosslinking step. The top glass slide is removed after polymerization, and the unpolymerized monomer is washed away (developed) with water, leaving a fine feature pattern of polyacrylamide hydrogel, which is used to produce the cross-linked polyacrylamide hydrogel. Further, lithographic techniques known in the semiconductor industry can be used to generate patterned gel structures. Light can be applied to discrete locations on the surface of a polyacrylamide hydrogel to activate specified regions for the attachment of an oligonucleotide, an antibody, an antigen, a hormone, hormone receptor, a ligand or a polysaccharide on the surface (e.g., a polyacrylamide hydrogel surface) of a solid support (see, for example, International Application, Publication No. WO 91/07087, incorporated by reference).

For hydrogel-based arrays using polyacrylamide, biomolecules can be prepared by forming an amide, ester or disulfide bond between the biomolecule and a derivatized polymer comprising the cognate chemical group. Covalent attachment of the biomolecule to the polymer is usually performed after polymerization and chemical cross-linking of the polymer is completed.

In some instances, it may be desirable to have etched polymer wells incorporated into the cell culture surface. Such surfaces have been described in the literature, however they require photolithography for the fabrication. While such a method could be used with this invention, other techniques can be used. The invention also provides for the creation of etched polymer wells using only a DNA-spotter, or similar device. In one embodiment, an acrylamide coated slide is created wherein N,N'-(1,2-Dihydroxyethylene)bis-acrylamide (DHEBA) is incorporated as a crosslinking agent in the polymer network instead of bis-acrylamide. The DNA spotter can then be used to deposit a mild solution of periodic acid which will dissolve the acrylamide network locally, thus creating a "microwell" (see FIG. 2A). The well can then be further modified by depositing proteins or pre-polymer solutions which can be gelled or immobilized in situ.

Controlled-release of soluble factors from a degradable polymer substrate has been demonstrated in the fields of drug delivery and biomimetic engineered surfaces. Typically, soluble factors are immobilized within a polymer matrix or hydrogel. As the matrix degrades, soluble factors are released into the environment. The degradation of the polymer, and thus the release kinetics, can be tailored by modifying the composition of the polymer or hydrogel. In one variation, growth factors are incorporated into poly(lactide-co-glycolide) (PLGA) microspheres. The GF-laden microspheres are then incorporated into a suitable matrix, such as PEG-hydrogel, PLGA, or acrylamide. FIG. 2D-F shows several possible implementations of this strategy in conjunction with ECM microarrays and microfluidic networks.

Either or both the spotted surface and microfluidic channel surface can be made to incorporate active or passive electronic components, such as resistive heating elements, photodiodes, light-emitting diodes, analog amplifiers, and digital processing. These components would allow for self contained cell-culture, and monitoring of cellular processes using in situ detection methods. In the simplest embodiment, this is accomplished by choosing silicon as the substrate of choice for either or both the spotted substrate and microfluidic channel substrate, and using standard silicon microelectronic fabrication techniques. FIG. 3e illustrates various concepts that could be incorporated into such a device.

As mentioned herein, in some instances the substrate may be modified to promote cellular adhesion and growth. For example, a glass substrate may be treated with protein (i.e., a peptide of at least two amino acids) such as collagen or fibronectin to assist cells in adhering to the substrate. In some embodiments, the proteinaceous material is used to define (i.e., produce) a microarray. The microarray produced by the protein serves as a "template" for formation of the cellular microarray. Typically, a single protein will be adhered to the substrate, although two or more proteins may be used to spot a substrate using a spotter device. Proteins that are suitable for use in modifying a substrate to facilitate cell adhesion include proteins to which specific cell types adhere under cell culture conditions. For example, hepatocytes are known to bind to collagen. Therefore, collagen is well suited to facilitate binding of hepatocytes. Other suitable proteins include fibronectin, gelatin, collagen type IV, laminin, entactin, and other basement proteins, including glycosaminoglycans such as heparin sulfate. Combinations of such proteins also can be used.

With regard to placing insoluble and/or soluble factors at specific locations, various micro-spotting techniques using computer-controlled plotters or even ink-jet printers have been developed to spot such factors at defined locations. One technique loads glass fibers having multiple capillaries drilled through them with different oligonucleotides loaded into each capillary tube. Microarray substrate, such as a glass microscope slide, is then stamped out much like a rubber stamp on each glass slide. Spotting techniques involve the precise placement of materials at specific sites or regions using automated techniques.

Conventional physical spotting techniques such as quills, pins, or micropipettors are able to deposit material on substrates in the range of 10 to 250 microns in diameter (e.g., about 100 spots/microwells per we of a 96 well culture plate). In some instances the density can be from 400 to 10000 spots per square centimeter, allowing for clearance between spots. Lithographic techniques, such as those provided by Affymetrix (e.g., U.S. Pat. No. 5,744,305, the disclosure of which is incorporated by reference herein) can produce spots down to about 10 microns square, with no clearance between spots, resulting in approximately 800,000 spots per square centimeter.

In some embodiments, materials (e.g., insoluble and/or soluble materials) are delivered (e.g. spotted) into at least one of the plurality of microwells in very small, e.g. nanoliter, increments using a spotting device. The spotting device may employ one or more piezoelectric pumps, acoustic dispersion, liquid printers, micropiezo dispensers, or the like to deliver such reagents to each of the microwells. In some embodiments, the spotting device comprises an apparatus and method like or similar to that described in U.S. Pat. Nos. 6,296,702, 6,440,217, 6,579,367, and 6,849,127.

Accordingly, an automated spotting device can be utilized, e.g. Perkin Elmer BioChip Arrayer™. A number of contact and non-contact microarray printers are available and may be used to dispense/print the soluble and/or insoluble materials on a substrate. For example, non-contact printers are available from Perkin Elmer (BioChip Arrayer™), Labcyte and IMTEK (TopSpot™), and Bioforce (Nanoarrayer™). These devices utilize various approaches to non-contact spotting, including piezo electric dispension; touchless acoustic transfer; en bloc printing from multiple microchannels; and the like. Other approaches include ink jet-based printing and microfluidic platforms. Contact printers are commercially available from TeleChem International (ArrayIt™). Non-contact printers are of particular interest because they are more compatible with deformable hydrogel surfaces and allow for simpler control over spot size via multiple dispensing onto the same location.

Non-contact printing will typically be used for the production of cellular microarrays. By utilizing a printer that does not physically contact the surface of substrate, no aberrations or deformities are introduced onto the substrate surface, thereby preventing uneven or aberrant cellular capture at the site of the spotted material. Such printing methods find particular use with hydrogel substrates.

Printing methods of interest, including those utilizing acoustic or other touchless transfer, also provide benefits of avoiding clogging of the printer aperture, e.g. where probe solutions have high viscosity, concentration and/or tackiness. Touchless transfer printing also relieves the deadspace inherent to many systems. The use of print heads with multiple ports and the capacity for flexible adjustment of spot size can be used for high-throughput microarray preparation.

The total number of spots on the substrate will vary depending on the number of different conditions (e.g., material combinations) to be explored, as well as the number of control spots, calibrating spots and the like, as may be desired. Generally, the pattern present on the surface of the support will comprise at least 2 distinct spots, usually about 10 distinct spots, and more usually about 100 distinct spots, where the number of spots can be as high as 50,000 or higher. The spot/microwell will usually have an overall circular dimension and the diameter will range from about 10 to 5000 µm (e.g., about 20 to 1000 µm).

By dispensing or printing onto the surfaces or into a microwell of multi-well culture plates, one can combine the advantages of the array approach with those of the multi well approach. Typically, the separation between tips in standard spotting device is compatible with both a 384 well and 96 well plate, one can simultaneously print each load in several wells. Printing into wells can be done using both contact and non-contact technology (as described above).

The methods and systems of the invention are useful to modulate the density of biological materials "spotted" on a cell culture substrate. For example, the maximum density of ECM molecules is dependent on several factors including: the concentration of stock solution, the solubility of ECM proteins, the porosity of the substrate or gel (e.g., polyacrylamide gel), and the mode of deposition (e.g., pin or piezoelectric). Controlling the amount/density of biological materials in a culture environment can modulate cell growth and differentiation. For example, a minimum surface density of integrin ligands is required for cell attachment and spreading, and is estimated to be as low as 1 ng/cm$^2$ for hepatocyte cells on laminin, fibronectin, collagen I, and collagen IV. Accordingly, the spotting device can be calibrated and used to provide specific amounts of insoluble and/or soluble biological materials to select "spots" or microwells.

The invention provides methods and systems useful for identifying optimal conditions for controlling cellular development and maturation. For example, the methods and systems of the invention are useful for identifying optimal conditions that control the fate of cells (e.g., differentiating stem cells into more mature cells, maintenance of self-renewal, and the like) by controlling and optimizing the extracellular and soluble microenvironment upon which the cells are cultured in parallel array fashion for rapid high throughput techniques.

A miniaturized cell culture microarray platform of the invention is useful for testing a multitude of soluble factors (e.g., growth factors, hormones, steroids and the like) and insoluble factors (e.g., extracellular matrix, cell adhesion proteins, glycoproteins and the like) individually and in combination using minimal reagents and a relatively small numbers of cells.

The invention utilizes robotic spotting technology to develop a robust, accessible method for forming cellular microarrays on, for example, an adherence material such as combinatorial extracellular matrix domains—that required no photolithographic 'cell micropatterning' tools or custom-built equipment and only small amounts of protein (~10 pg) per experimental condition. As used herein, the term "microarray" refers to a plurality of addressed or addressable locations (e.g., microwells). The location of each of the microwells or groups of microwells in the array is typically known, so as to allow for identification and, as more fully described below, assay of particular changes in expression, morphology, and the like.

With the advent of DNA robotic spotting technology, it is now possible to routinely deliver nanoliter volumes of many different materials, from interfering RNA, to peptides, to biomaterials at precise locations on a microarray substrate. To date, techniques that use spotted microarrays for cell culture have not been appropriate for manipulation of ECM material due to, for example, incompatible process conditions for ECM protein spotting, extensive customization of spotting equipment, or lack of pattern fidelity (i.e. cell localization) over time.

In one aspect, the invention provides methods and systems that overcome these limitations by, for example, modifying the printing buffer used in a spotting device to allow for ECM deposition, and identifying microarray substrates that permit ECM immobilization. For example, in one aspect, the substrate is a hydrogel surface that maintains spatially confined cellular islands through the use of microwell generation in a hydrogel material.

Figure 3:
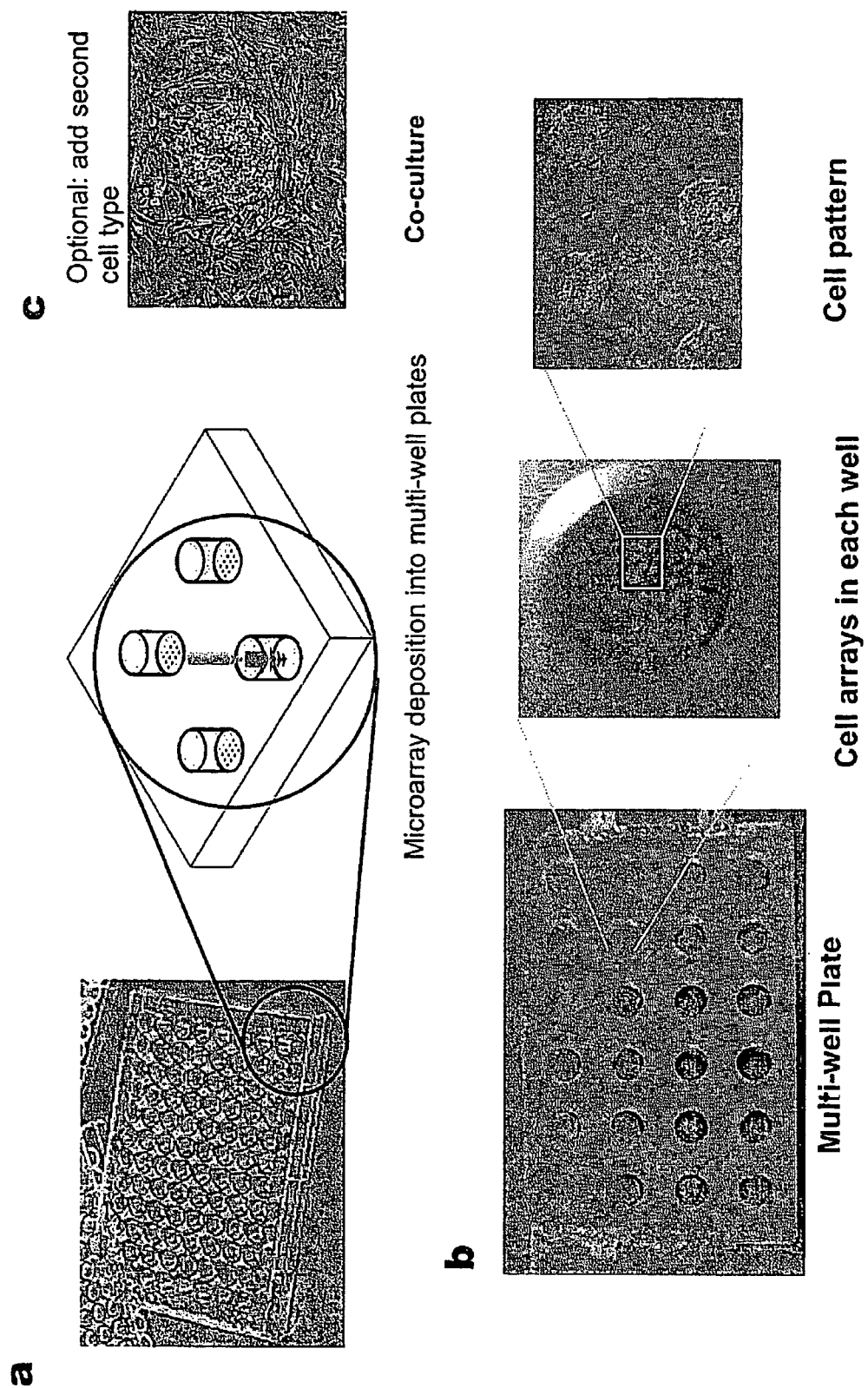
FIG. 3A-C depicts photomicrographs of microarrays of the invention generated within multichamber cell culture plates. (A) Shows a schematic of a microarray within a 96 well plate. (B) Shows a multi-well plate with subsequent magnification depicting the patterning of the cellular array in each well. (C) Shows a micrograph of a co-culture of a first cell type and a second cell type in the system of the invention.
Figure 4:
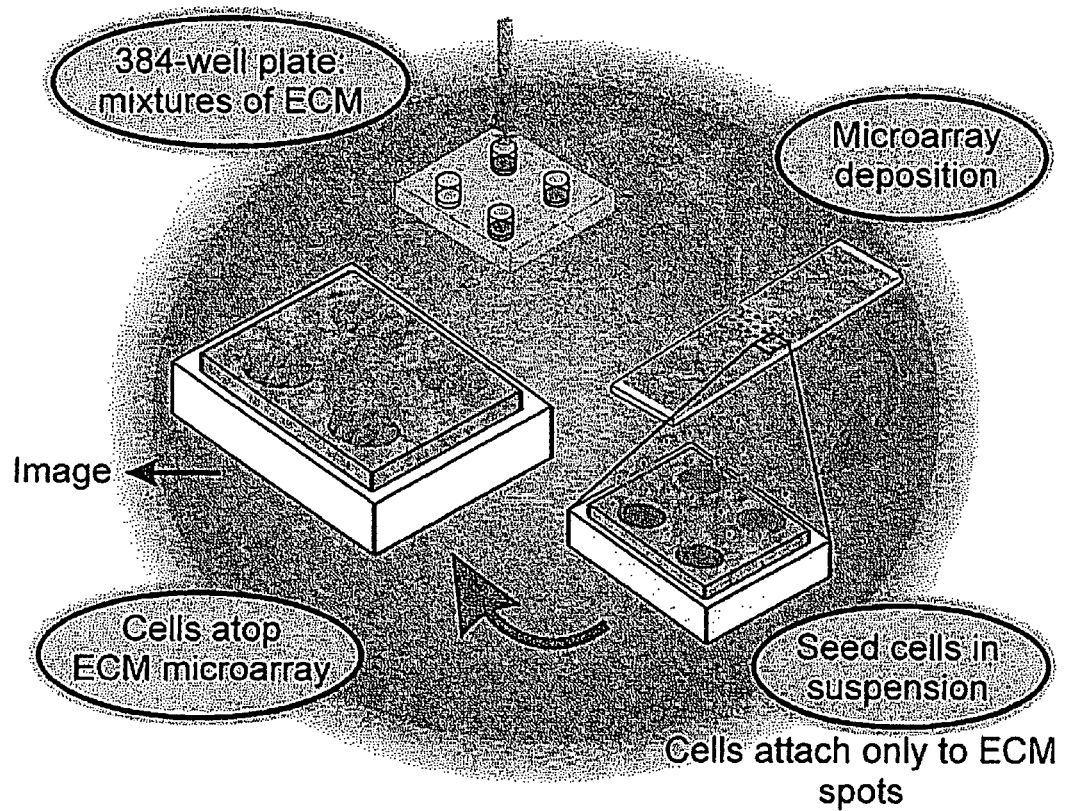
FIG. 4 shows a method of the invention, whereby a microarray is prepared and seeded with cells that attach at discrete "spots" in the array. The array can then be treated or cultured under desired conditions and then imaged or analyzed.
Figure 5:
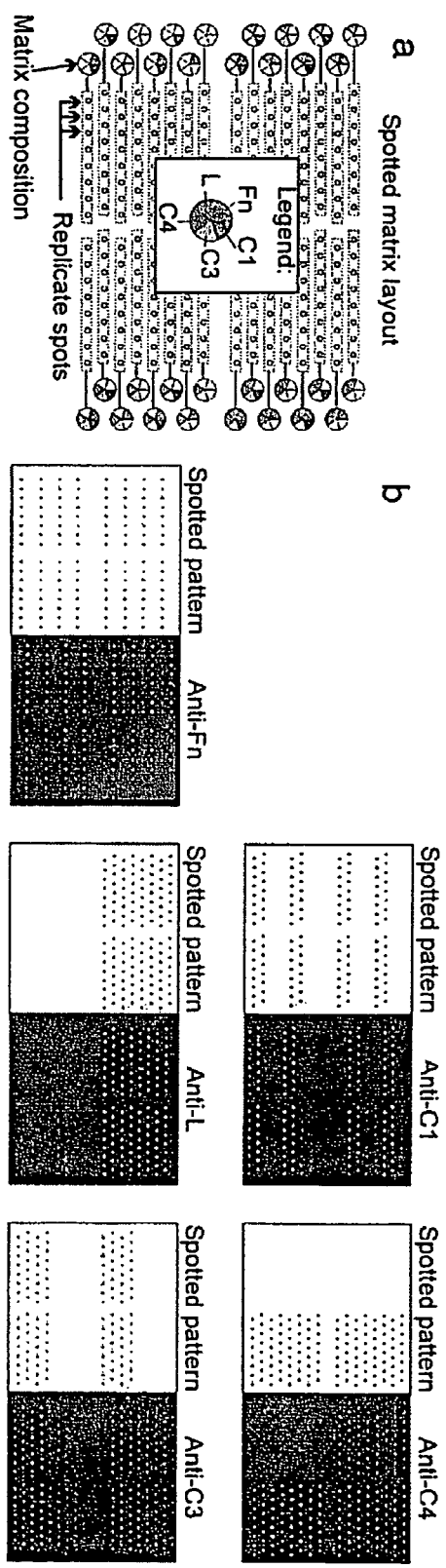
FIG. 5A-B shows the characterization of an ECM microarray by indirect immunofluorescence. (A) Shows the composition and layout of each row. 32 conditions in 8 replicates each were used. The spotting solution concentration of each ECM molecule, when present in a mixture, was 100 μg/mL. (B) Shows the correlation of specified array compositions and immunofluorescence of replicate arrays demonstrates presence and immunoreactivity of all 5 ECM components with minimal carryover between conditions. C1, collagen I; C3, collagen III; C4, collagen IV; L, laminin; Fn, fibronectin.
Figure 6:
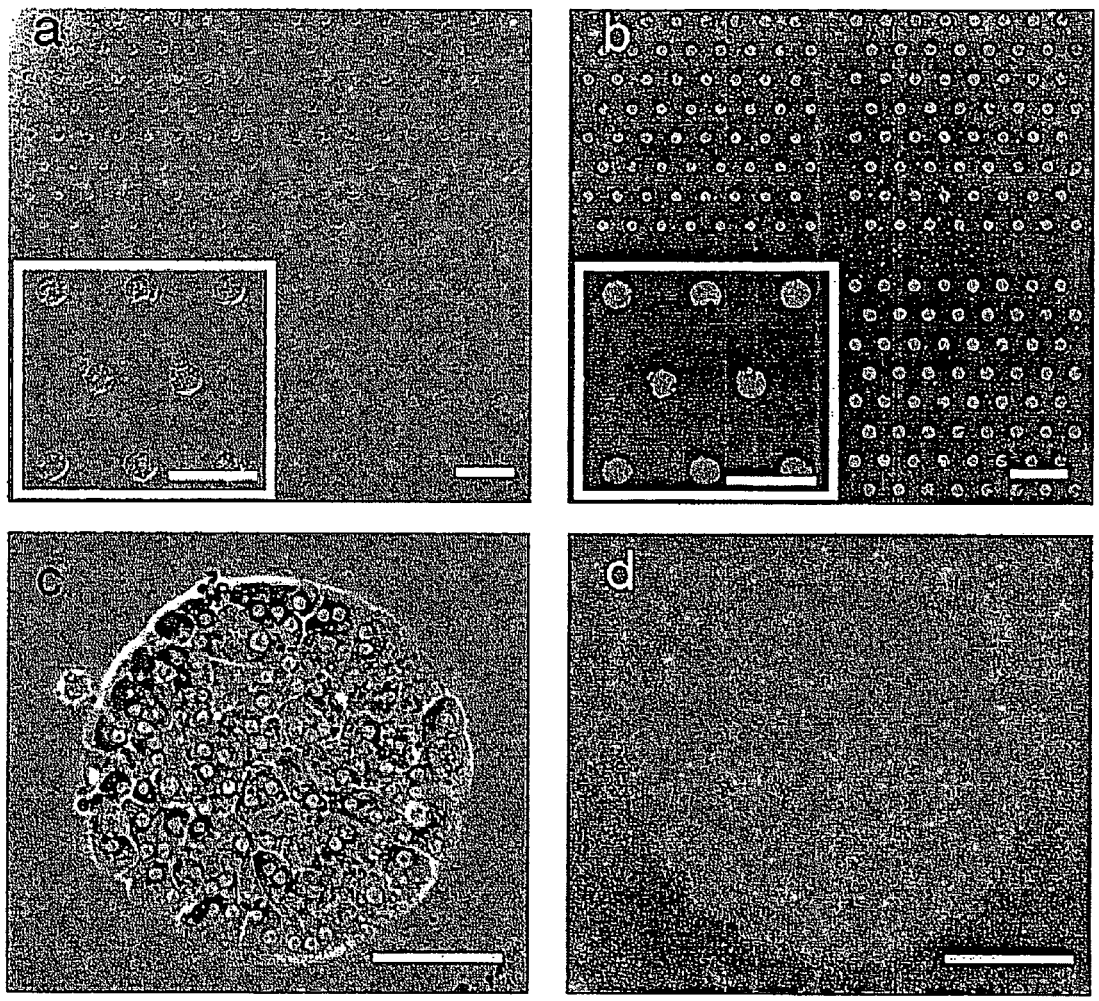
FIG. 6A-D shows primary rat hepatocytes on ECM microarrays. (A) Shows a Hoffman contrast montage image of the ECM microarray after 24 hours of culture in 10% serum (magnified view in inset). Hepatocytes are well spread, have bright intercellular borders and distinct nuclei, and spread to occupy the full ECM island in culture conditions. (B) Live/dead stains of hepatocytes using Calcein AM/ethidium homodimer depicts ~95% viability at 24 hours (magnified view in inset). Scale bars, 1 mm (inset scale bars, 500 µm). (C) High magnification phase contrast and fluorescent images. (D) A single island (Calcein AM, DAPI). Scale bars, 50 µm.

The methods and systems of the invention are useful for spotting substantially purified or mixtures of biological proteins, nucleic acids and the like (e.g., collagen I, collagen III, collagen IV, laminin, and fibronectin) in various combinations on a standard cell culture substrate (e.g., a microscope slide) using off-the-shelf chemicals and a conventional DNA robotic spotter (FIGS. 1 and 3).

Cell culture is a highly empirical field, thus this platform allows for a multitude of insoluble factors (e.g. extracellular matrix, biomaterials), tethered soluble factors (e.g., growth factors), or mixtures of insoluble and soluble cues to be tested in parallel on a small scale.

The term "adherence material" is a material deposited on a substrate or chip or within a microwell in an array for which a cell or microorganism has some affinity, such as a binding agent. The material can be deposited in a domain, microwell or "spot". The material and a cell or microorganism interact through any means including, for example, electrostatic or hydrophobic interactions, covalent binding or ionic attachment. The material may include, but is not limited to, antibodies, proteins, peptides, nucleic acids, peptide aptamers, nucleic acid aptamers, or cellular receptors.

A "plurality of domains" or "spots" or "microwells" includes more than one discrete domain or spot of an adherence material that is deposited onto a solid support, or a material that is deposited onto the surface of a solid support. In one embodiment the solid support and the surface will form a chip. Different materials that specifically interact with different cells or microorganisms may be deposited in separate and discrete domains on or in the substrate surface.

In one embodiment, the invention provides a surface comprising multiple distinct cell culture domains (microwells) of arbitrary protein or polymer composition and size by using robotic spotting technology (e.g., a DNA spotting device or a similar device), to transfer nanoliter quantities of material onto a culture substrate (e.g., glass, silicon, polymer or other biocompatible material used in cell culture) at desired locations.

In one embodiment, one or more desired biological materials are deposited as discrete "spots" on a culture substrate surface. In one aspect, each spot comprises a different biological material composition. In another aspect, each spot comprises the same biological material composition. Cells cultured on the spots may be the same or different. For example, a defined ECM material is deposited as discrete spots onto a culture substrate surface. Cells are then contacted with the substrate and cultured under desired culture conditions. Where the spots comprise different biological materials, the cells experience different stimuli while being cultured simultaneously but maintained in distinct spatial domains creating a cellular array.

The spotted surface can also be bonded with a molded polymer or etched surface such that a microfluidic network is created with a plurality of channels and chambers. The fluidic network can be engineered to mix soluble factors and deliver them to addressable locations on the microarrayed surface. This would allow for cell culture media additives to be modulated in an efficient manner as only small volumes would be required.

A microfluidic network can be fabricated through micromolding of an elastomer against a negative relief of the microchannels, or by selectively etching a surface of a material such as glass or silicon. This network is bonded to the protein microspotted substrate. The microchannels can be designed to deliver specific concentrations and combinations of soluble factors to various locations on the array.

Either or both the spotted surface and microfluidic channel surface can be made to incorporate active or passive electronic components, such as resistive heating elements, photodiodes, light-emitting diodes, analog amplifiers, and digital processing. These components would allow for self contained cell-culture, and monitoring of cellular processes using in situ detection methods. In the simplest embodiment, this is accomplished by choosing silicon as the substrate of choice for either or both the spotted substrate and microfluidic channel substrate, and using standard silicon microelectronic fabrication techniques.

Microfluidic channels may be used in the methods of the invention to deliver media and/or reagents to cells in microwells 50. The microfluidic channels may be part of the substrate 10 or may be further etched or coated onto gel pad 20 (see, e.g., FIGS. 2D-F). Typically, the system comprises a culture microwell having an inlet and an outlet designed to allow fluid to flow across/through the microwell. Cells and/or biological material (e.g., ECM) can be disposed between and in fluid communication with the inlet and outlet. The at least one inlet and one outlet can comprise valves to control fluid flow.

Thus, devices of the invention can include at least one flow channel that allows fluid flow from an inlet to an outlet. As will be appreciated by those in the art, the flow channels may be configured in a wide variety of ways, depending on the use of the channel. For example, a single flow channel may be separated into a variety of smaller or similarly sized channels, such that the original sample is divided into discrete subsamples for parallel processing or analysis (see, e.g., FIG. 2D-F). Alternatively, several flow channels may feed together into a single channel. As will be appreciated by those in the art, there are a large number of possible configurations; what is important is that the flow channels allow the movement of sample and reagents from one part of the array to another.

In another aspect of the invention, the system comprises at least one pump. These pumps can be any type of pump device including electrode based pumps. Electromechanical pumps can be used in the systems of the invention, e.g. based upon capacitive, thermal, and piezoelectric actuation. Suitable "on chip" pumps include, but are not limited to, electroosmotic (EO) pumps and electrohydrodynamic (EHD) pumps; these electrode based pumps have sometimes been referred to in the art as "electrokinetic (EK) pumps". In another aspect, the pumps are external to the microfluidic channel. In this aspect, the pump may be a peristaltic pump, syringe pump or other pump commonly used in the art.

A microfluidic flow regulator can be used in the system and methods of the invention, such as one or more of the micropumps described herein, for controlling the flow rate. Such pumps may include, for example, a microelectromechanical (MEMS) microfluidic pump. The micropump can be operated at a predetermined frequency, which can be either substantially constant or modulated depending upon the requirements of the system (e.g., the cellular metabolism, metabolite delivery and the like).

In another aspect of the invention, microarray devices of the invention may include at least one fluid valve that can control the flow of fluid into or out of a microarray device or divert the flow into one or more channels. A variety of valves are known in the art. For example, in one embodiment, the valve may comprise a capillary barrier.

In yet another embodiment, sealing ports may be used to allow the introduction of fluids, including samples, into the array of the invention, with subsequent closure of the port to avoid the loss of the sample.

The devices of the invention can include at least one storage modules for assay reagents (e.g., buffer, sample, and culture media). These may be fluidly connected to other modules of the system using flow channels and may comprise wells or chambers, or extended flow channels.

The microfluidics can be utilized to deliver test analytes to cellular microarrays of the invention. Analytes include organic and inorganic molecules, including biological molecules. For example, the analyte may be an environmental pollutant (including pesticides, insecticides, toxins, and the like); a chemical (including solvents, polymers, organic materials, and the like); therapeutic molecules (including therapeutic and abused drugs, antibiotics, and the like); biological molecules (including, e.g., hormones, cytokines, proteins, lipids, carbohydrates, cellular membrane antigens and receptors (neural, hormonal, nutrient, and cell surface receptors) or their ligands); whole cells (including prokaryotic and eukaryotic cells; viruses (including, e.g., retroviruses, herpesviruses, adenoviruses, lentiviruses); spores; and the like.

Regarding the cell culture aspect, one cell type of a plurality of cell types can be used in the microarrays of the disclosure. For example, cultures of two cell types can be performed thus allowing for co-culture of two cell types. For example, the culture surface surrounding the a first spot can be modified such that cells cannot attach to or migrate to the regions surrounding the spot. In this manner, mono-culture or co-culture involving multiple cell types and multiple ECM coatings can be tested in a single 96-well plate.

The type of biological materials (e.g., ECM materials) deposited in the microarray will be determined, in part, by the cell type or types to be cultured. For example, ECM molecules found in the hepatic microenvironment are useful in culturing hepatocytes, the use of primary cells, and a fetal liver-specific reporter ES cell line. The liver has heterogeneous staining for collagen I, collagen III, collagen IV, laminin, and fibronectin. Hepatocytes display integrins $\beta 1$, $\beta 2$, $\alpha 1$, $\alpha 2$, $\alpha 5$, and the nonintegrin fibronectin receptor Agp110 in vivo. Cultured rat hepatocytes display integrins $\alpha 1$, $\alpha 3$, $\alpha 5$, $\beta 1$, and $\alpha 6 \beta 1$, and their expression is modulated by the culture conditions. It will be recognized that the initial material used in the array will be modulated by cellular interactions. For example, interaction with ECM is known to modulate matrix metalloproteinase expression, integrin activity, and matrix expression.

ECM and growth factor interactions, which can be positive or negative, have been reported in multiple contexts. In addition to the described crosstalk between integrin and growth factor signaling, crosstalk exists among matrix molecules. For example, it has been reported that collagen induced release of IL-1 through binding integrin $\alpha 7 \beta 1$ in human blood mononuclear cells is potentiated by fibronectin binding to $\alpha 5 \beta 1$. Similarly, endothelial cell attachment to fibronectin via $\alpha 5 \beta 1$ integrin reportedly potentiates $\alpha v \beta 3$-mediated migration on vitronectin. In this context, the invention and the results presented below with hepatocytes suggest that integrin crosstalk may explain the apparent antagonistic interactions among collagen III and laminin, and collagen IV and fibronectin; a hypothesis that is testable by the methods and systems of the invention.

The invention is advantageously used for performing assays on microchips/biochips. Microchips (also sometimes referred to as biochips) encompass substrates containing arrays or microarrays, typically ordered arrays and most commonly ordered, addressable arrays, of a biological material or a mixture of biological materials.

One useful feature of such chips is the manner in which the arrayed biomolecules are attached to the surface of the chip's substrate. Conventionally such procedures involve reaction steps, including chemical modification of the solid support itself. In some aspects, modification of the support surface or modification of the gel polymer is useful to provide a chemical functionality capable of forming sufficient bonding.

The effect of soluble and insoluble factors/test analytes have on cells in a microarray can be probed for a specific marker, examined for morphology, and the like. For example, the array can be probed for the state of differentiation using various techniques including in situ hybridization, antigenic recognition (intracellular or cell membrane), in situ PCR, or an artificial DNA-reporter construct such as GFP or beta-galactosidase. The cell array can be assessed using fluorescent microscopy, high resolution light microscopy, a confocal laser scanner (such as those commonly used for DNA microarray applications), fluorescence and absorbance plate readers, scanners, or other such equipment. In many aspect, the measurements will be made by automated microscopes, plate readers and the like. In this manner, "optimal" culture conditions, as defined by the user, can be identified for closer examination and testing using more conventional techniques.

Fixation of cells generally leads to disruption of cellular architecture, loss of antigen recognition, and loss of soluble matter from "leaky" cells during the numerous washing steps. As an alternative, cellular arrays can be freeze transferred to a nitrocellulose membrane, a process known in the field as "cytocoherent transfer". This process preserves the spatial (X-Y) distribution of proteins, but significantly compresses the 3D data into a more 2D configuration. The proteins are much better retained by the nitrocellulose membrane, which also provides excellent access to the antigenic sites that can be probed using immunochemical detection methods. Cytotransfer is accomplished by cryogenically freezing the cell culture array, followed by placing it in contact with a thin nitrocellulose (or other material) membrane. This act initiates a "thaw transfer" of the biological material to the membrane. This process is advantageous for several reasons: it does not require fixatives, small cytosolic molecules are directly transferred to the membrane (whereas they might be washed away during fixation and washing), the membrane provides excellent antigenic access, and the 3D spatial protein information is somewhat compressed into a more 2D, but accurate in the planar direction, representation. Compressing the information into a more 2D format is advantageous from a quantification standpoint. Typically confocal laser scanners are used to quantify microarray format material. The 3D nature of cell cultures presents a difficulty for such equipment, unless multiple z-planes are imaged and analyzed. Often, the 3D information is not of practical value, and a 2D representation would be sufficient. Compressing the 3D cellular protein presentation into a more 2D representation prior to detection thus alleviates the need to image multiple z-planes using a such a confocal device. Alternatively, the same technique can be used in conjunction with luminescent assays simply because of the advantage of improved cellular protein retention in the membrane, which results in an increased signal. Such techniques are further described in McGrath et al., Bio-Techniques 11:352-361, 1991.

Cells cultured on microarrays of the disclosure may be used to study cell and tissue morphology. For example, enzymatic and/or metabolic activity may be monitored in the culture by fluorescence or spectroscopic measurements on a conventional microscope. In one aspect, a fluorescent metabolite in the fluid/media is used such that cells will fluoresce under appropriate conditions (e.g., upon production of certain enzymes that act upon the metabolite, and the like). Alternatively, recombinant cells can be used in the cultures system, whereby such cells have been genetically modified to include a promoter or polypeptide that produces a therapeutic or diagnostic product under appropriate conditions (e.g., upon zonation or under a particular oxygen concentration). For example, a hepatocyte may be engineered to comprise a GFP (green fluorescent protein) reporter on a P450 gene (CYP1A1). Thus, if a drug activates the promoter, the recombinant cell fluoresces. This is useful for predicting drug-drug interactions that occur due to upregulation in P450s.

Embryonic stem cells are a potential source of differentiated cells that could be used in cell therapy, drug discovery, and basic research. Current methods for differentiating embryonic stem cells in vitro are generally inefficient (~1%) for generating specific lineages, and rely on the use of heterogeneous cell aggregates called embryoid bodies. Exceptions to this generalization are a few rare reports of efficient monolayer culture methods, underscoring the importance of a tightly regulated environment for efficient lineage-specific differentiation. While most studies focus on growth factors, the importance of ECM in developmental processes has increasingly been recognized. In vitro, undifferentiated mouse ES cells express integrins $\alpha 6$, $\beta 1$, $\beta 4$, $\beta 5$, laminin receptor 1, and dystroglycan; thus poised to receive signals from ECM. Given that stem cell differentiation has historically been a largely empirical field, a parallelized culture platform is of benefit. Monitoring can be performed using specific markers or ubiquitous cellular constituents such as actin and keratin.

In one aspect, the microarray utilizes ECM protein microarrays to study and obtain ES differentiation in the context of the liver. In vitro differentiation of I114 mouse embryonic reporter stem cells as embryoid bodies induces reporter expression that coincides with endodermal gene upregulation, and co-localization with alpha-fetoprotein and albumin protein. As such, it serves as a tool to study early hepatic specification in vitro. Culturing ES cells as 3-dimensional aggregates greatly improves the frequency of differentiation to somatic lineages; however, embryoid bodies are seldom uniform in size. The invention provided methods that produce uniform, spatially confined, 3-D growth of ES cells cultured on ECM microarrays with LIF. The microarray provides a confined domain that result in appropriate differentiation and growth. In contrast, culturing with RA resulted in a noticeable flattening of the cellular island morphology likely due to induction of differentiation, a reduction in proliferation, and therefore less expansion in the z-direction. From image analysis reporter activity in day 9 EB's was estimated at <1% and even less in monolayer cultures. In contrast, the day 3 RA-induced micro-cultures exhibited up to 16.8%±5.5% (N=8) of the island area showing reporter activity when cultured on optimal ECM microenvironments. Moreover, an approximate 140-fold increase was detected in $\beta$-galactosidase signal from the least efficient condition (laminin only) to the most efficient (laminin+collagen I+fibronectin). Thus, the invention provides methods and systems to investigate and identify how complex ECM enhance reporter activity providing valuable insight on how to drive in vitro differentiation more efficiently.

The invention described herein provides a substrate that can be read or analyzed by a variety of methods including, but not limited, to fluorescence, surface plasmon resonance, mass spectrometry, quartz crystal resonance, electron microscopy and scanning probe microscopy. In one aspect scanning probe microscopy (SPM) such as atomic force microscopy (AFM). Use of an AFM or another type of SPM creates a methodology for a simple rapid, sensitive and high throughput method for detection of microorganisms, pathogens, biological matter, viruses, or microparticles (Moloney et al., 2002, Ultramicroscopy 91 pp. 275-279). This method can be used to detect changes in a spot sample. Additionally, fluorescence or other methods commonly practiced for detection of biological events can be employed in the methods and systems of the invention.

The invention provides technology that can be useful for a variety of purposes, such as determining the appropriate culture conditions for differentiating stem cells into more mature cells, studying cell-matrix and growth factor interactions in a systematic manner, and potentially screening new drug molecule candidates for their effects on cells in vitro by immobilizing small volumes in degradable matrices for sustained release. Additionally, the platform can be extended for use with non-stem cells, such as primary cells (e.g. hepatocytes, fibroblasts), genetically modified cells, and transformed or cancerous cell types.

A number of uses of the methods and systems will be readily apparent to one of skill in the art. For example, stem cell therapeutic companies could use such technology to optimize differentiation protocols for specific lineages. Life-science or pharmaceutical companies could use such technology for optimizing in vitro production of recombinant proteins. Pharmaceutical companies could use a miniaturized cell culture platform to test toxicity of potential drug compounds in a parallel manner using minimal reagents. Researchers could use such a platform to test the effects of insoluble or tethered soluble and insoluble cues on cellular differentiation.

The culture system and microarrays of the disclosure can be used in a wide variety of applications. These include, but are not limited to, screening compounds, growth/regulatory factors, pharmaceutical compounds, and the like, in vitro; elucidating the mechanisms of certain diseases; studying the mechanisms by which drugs and/or growth factors operate; diagnosing and monitoring cancer in a patient; the production of biological products, to name a few.

The methods and systems of the disclosure may be used to in vitro to screen a wide variety of compounds, such as cytotoxic compounds, growth/regulatory factors, pharmaceutical agents, and the like, to identify agents that modify cell (e.g., hepatocyte) function and/or cause cytotoxicity and death or modify proliferative activity or cell function. For example, the culture system may be used to test adsorption, distribution, metabolism, excretion, and toxicology (ADMET) of various agents. The activity of a compound can be measured by its ability to damage or kill cells in culture or by its ability to modify the function of the cells (e.g., in hepatocytes the expression of P450, and the like). This may readily be assessed by vital staining techniques, ELISA assays, immunohistochemistry, and the like. The effect of growth/regulatory factors on the cells (e.g., hepatocytes, endothelial cells, epithelial cells, pancreatic cells, astrocytes, muscle cells, cancer cells) may be assessed by analyzing the cellular content of the culture, e.g., by total cell counts, and differential cell counts or by metabolic markers such as MTT and XTT. This may also be accomplished using standard cytological and/or histological techniques including the use of immunocytochemical techniques employing antibodies that define type-specific cellular antigens. The effect of various drugs on normal cells cultured in the culture system may be assessed. For example, drugs that affect cholesterol metabolism, e.g., by lowering cholesterol production, could be tested on a liver culture system.

The cytotoxicity to cells in culture (e.g., human hepatocytes) of pharmaceuticals, anti-neoplastic agents, carcinogens, food additives, and other substances may be tested by utilizing the microfluidic microarrays of the invention.

The invention provides a screening method comprising, generating a microarray on a substrate using a spotting device (e.g., a DNA spotting device) or similar device. A material spotted by the device may include soluble and/or insoluble factors that have known activity or effects on cells or may comprise factors having unknown activity of effects on cells. Cells are then contacted with the micro-spot array and a stable, growing culture is established. The cells may then be examined or alternatively, the cells are exposed to varying concentrations of a test agent. After incubation, the culture is examined by phase microscopy to determine the effect of the material and/or test agent on a cell's morphology, growth, activity, and the like. Cytotoxicity testing can be performed using a variety of supravital dyes to assess cell viability in the liver culture system, using techniques well-known to those skilled in the art.

Similarly, the beneficial effects of drugs or biologics may be assessed using the microarray system. For example, growth factors, hormones, or drugs which are suspected of having the ability to enhance cell or tissue function, formation or activity can be tested. In this case, stable cultures are exposed to a test agent. After incubation, the cultures are examined for viability, growth, morphology, cell typing, and the like, as an indication of the efficacy of the test substance. Varying concentrations of the drug may be tested to derive a dose-response curve.

The culture systems of the disclosure may be used as model systems for the study of physiologic or pathologic conditions and to optimize the production of a specific protein. For example, in a specific embodiment, a parenchymal cell culture (e.g., a liver culture) system can be optimized to act in a specific functional manner as described herein by spotting defined soluble and/or insoluble factors.

The microarray culture system may also be used to aid in the diagnosis and treatment of malignancies and diseases. For example, a biopsy of a tissue (such as, for example, a liver biopsy) may be taken from a subject suspected of having a malignancy or other disease or disorder. The biopsy cells can then be cultured under appropriate conditions (e.g., defined factors spotted on an array) where the activity of the cultured cells can be assessed using techniques known in the art. In addition, such biopsy cultures can be used to screen agent that modify the activity in order to identify a therapeutic regimen to treat the subject. For example, the subject's tissue culture could be used in vitro to screen cytotoxic and/or pharmaceutical compounds in order to identify those that are most efficacious; i.e. those that kill the malignant or diseased cells, yet spare the normal cells. These agents could then be used to therapeutically treat the subject.

Similarly, the beneficial effects of drugs may be assessed using a microarray in vitro; for example, growth factors, hormones, drugs which enhance hepatocyte formation or activity can be tested. In this case, microarray cultures may be exposed to a test agent. After incubation, the microarray cultures may be examined for viability, growth, morphology, cell typing, and the like as an indication of the efficacy of the test substance. Varying concentrations of the drug may be tested to derive a dose-response curve.

In one aspect, the study of hepatocyte function, differentiation, growth and metabolism can be examined. Isolated human hepatocytes are highly unstable in culture and are therefore of limited utility for studies on drug hepatotoxicity, drug-drug interaction, drug-related induction of detoxification enzymes, and other liver-based phenomena. The alternative approach is to employ animal experimentation to study the liver's response; however, there are many well-documented differences between animal and human metabolism that lead to inconclusive or inaccurate interpretation of animal data for human applications. The disclosure provides a micro-scale model of human liver cell and/or tissue that can be utilized for pharmaceutical drug development, basic science research, and in the development of tissue for transplantation.

In one aspect, micropatterned cultures comprising parenchymal cells and stromal cells are used in the methods and systems of the invention. For example, islands of material (e.g., protein material—soluble or insoluble) can be generated on a substrate to form an array. Each island may comprise the same material or an array of patterned different material. In some cases, adjacent islands comprise different materials that are directed to a particular cell type to be studied. In this manner and array of cell-types may be simultaneous cultured. For example, the substrate is modified and prepared such that stromal cells are interspersed with the parenchymal cells. Using a DNA spotter device, the substrate is modified to provide for spatially arranging parenchymal cells (e.g., human hepatocytes and supportive stromal cells (e.g., fibroblasts)) in a miniaturizable format. Specifically, parenchymal cells (e.g., hepatocytes) can be prepared in islands surrounded by stromal cells (e.g., fibroblast such as murine 3T3 fibroblasts). Furthermore, parenchymal cell function may be modified by altering the pattern configuration.

Using micropatterning of co-cultures and reagents can lead to a cell or tissue model that can be optimized for specific physiologic functions including, for example, synthetic, metabolic, or detoxification function (depending on the function of interest) in hepatic cell cultures.

In one aspect, the system utilizes co-cultures of cells in which at least two types of cells are configured in a micropattern on a substrate. By using micropatterning techniques to modulate the extent of heterotypic cell-cell contacts. In addition, co-cultures (both micropatterned co-cultures and non-micropatterned co-cultures) have improved stability and thereby allow chronic testing (e.g., chronic toxicity testing as required by the Food and Drug Administration for new compounds). Because micropatterned co-cultures are more stable than random cultures the use of co-cultures and more particularly micropatterned co-cultures provide a beneficial aspect to the cultures systems of the disclosure. Furthermore, because drug-drug interactions often occur over long periods of time the benefit of stable co-cultures allows for analysis of such interactions and toxicology measurements.

Typically, in practicing the methods of the disclosure, the cells are mammalian cells, although the cells may be from two different species (e.g., pigs, humans, rats, mice, and the like). The cells can be primary cells, stem cells, or they may be derived from an established cell-line. Although any cell type that adheres to a substrate can be used in the methods and systems of the disclosure (e.g., parenchymal and/or stromal cells), exemplary cell include, hepatocytes, epithelial cells, endothelial cells, pancreatic cells, muscle cells, neuronal cells, etc.

Cells useful in the methods and to populate a micro-spotted substrate or microwell of the disclosure are available from a number of sources including commercial sources. For example, hepatocytes may be isolated by conventional methods (Berry and Friend, 1969, J. Cell Biol. 43:506-520) which can be adapted for human liver biopsy or autopsy material. Typically, a canula is introduced into the portal vein or a portal branch and the liver is perfused with calcium-free or magnesium-free buffer until the tissue appears pale. The organ is then perfused with a proteolytic enzyme such as a collagenase solution at an adequate flow rate. This should digest the connective tissue framework. The liver is then washed in buffer and the cells are dispersed. The cell suspension may be filtered through a 70 μm nylon mesh to remove debris. Hepatocytes may be selected from the cell suspension by two or three differential centrifugations.

For perfusion of individual lobes of excised human liver, HEPES buffer may be used. Perfusion of collagenase in HEPES buffer may be accomplished at the rate of about 30 ml/minute. A single cell suspension is obtained by further incubation with collagenase for 15-20 minutes at 37° C. (Guguen-Guillouzo and Guillouzo, eds, 1986, "Isolated and Culture Hepatocytes" Paris, INSERM, and London, John Libbey Eurotext, pp. 1-12; 1982, Cell Biol. Int. Rep. 6:625-628).

Hepatocytes may also be obtained by differentiating pluripotent stem cell or liver precursor cells (i.e., hepatocyte precursor cells). The isolated hepatocytes may then be used in the culture systems described herein.

Stromal cells include, for example, fibroblasts obtained from appropriate sources as described further herein. Alternatively, the stromal cells may be obtained from commercial sources or derived from pluripotent stem cells using methods known in the art.

Fibroblasts may be readily isolated by disaggregating an appropriate organ or tissue which is to serve as the source of the fibroblasts. This may be readily accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, dispase and the like. Mechanical disruption can also be accomplished by a number of methods including, but not limited to, the use of grinders, blenders, sieves, homogenizers, pressure cells, or insonators. For a review of tissue disaggregation techniques, see Freshney, Culture of Animal Cells. A Manual of Basic Technique, 2d Ed., A. R. Liss, Inc., New York, 1987, Ch. 9, pp. 107-126.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis, fluorescence-activated cell sorting, and the like. For a review of clonal selection and cell separation techniques, see Freshney, Culture of Animal Cells. A Manual of Basic Techniques, 2d Ed., A. R. Liss, Inc., New York, 1987, Ch. 11 and 12, pp. 137-168.

The isolation of fibroblasts can, for example, be carried out as follows: fresh tissue samples are thoroughly washed and minced in Hanks balanced salt solution (HBSS) in order to remove serum. The minced tissue is incubated from 1-12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts can then be used in the culture systems of the disclosure.

For example, and not by way of limitation, endothelial cells may be isolated from small blood vessels of the brain according to the method of Larson et al. (1987, Microvasc. Res. 34:184) and their numbers expanded by culturing in vitro using the bioreactor system of the disclosure. Silver staining may be used to ascertain the presence of tight junctional complexes specific to small vessel endothelium and associated with the "barrier" function of the endothelium.

Suspensions of pancreatic acinar cells may be prepared by an adaptation of techniques described by others (Ruoff and Hay, 1979, Cell Tissue Res. 204:243-252; and Hay, 1979, in, "Methodological Surveys in Biochemistry Vol. 8, Cell Populations." London, Ellis Hornwood, Ltd., pp. 143-160). Briefly, the tissue is minced and washed in calcium-free, magnesium-free buffer. The minced tissue fragments are incubated in a solution of trypsin and collagenase. Dissociated cells may be filtered using a 20 µm nylon mesh, resuspended in a suitable buffer such as Hanks balanced salt solution (HBSS), and pelleted by centrifugation. The resulting pellet of cells can be resuspended in minimal amounts of appropriate media and inoculated onto a substrate for culturing in the bioreactor system of the disclosure. The pancreatic cells may be cultured with stromal cells such as fibroblasts. Acinar cells can be identified on the basis of zymogen droplet inclusions.

Cancer tissue may also be cultured using the methods and bioreactor culture system of the disclosure. For example, adenocarcinoma cells can be obtained by separating the adenocarcinoma cells from stromal cells by mincing tumor cells in HBSS, incubating the cells in 0.27% trypsin for 24 hours at 37° C. and further incubating suspended cells in DMEM complete medium on a plastic petri dish for 12 hours at 37° C. Stromal cells selectively adhered to the plastic dishes.

In addition, combinations of cells include, without limitation: (a) human hepatocytes (e.g., primary hepatocytes) and fibroblasts (e.g., normal or transformed fibroblasts, such as NIH 3T3-J2 cells); (b) hepatocytes and at least one other cell type, particularly liver cells, such as Kupffer cells, Ito cells, endothelial cells, and biliary ductal cells; and (c) stem cells (e.g., liver progenitor cells, oval cells, hematopoietic stem cells, embryonic stem cells, and the like) and human hepatocytes and/or other liver cells and a stromal cell (e.g., a fibroblast). Other combination of hepatocytes, liver cells, and liver precursor cells.

In another aspect, certain cell types have intrinsic attachment capabilities, thus eliminating a need for the addition of serum or exogenous attachment factors. Some cell types will attach to electrically charged cell culture substrates (e.g., electrically charged spots or microwells) and will adhere to the substrate via cell surface proteins and by secretion of extracellular matrix molecules. Fibroblasts are an example of one cell type that will attach to cell culture substrates under these conditions.

In one embodiment, user defined ECM protein mixtures are deposited as discrete "spots" into each well of a 96-well, or similar, culture plate (FIG. 2B). Cells can then be cultured in the wells, and adhere to the protein spotted domains preferentially under appropriate conditions, creating a cellular array. If desired, a second cell type can then be added to the culture regions unoccupied by the first cell type, thus allowing for co-culture of two cells types. Alternatively, the culture surface surrounding the protein spots can be modified such that cells cannot attach to or migrate to the regions surrounding the protein spots. In this manner, mono-culture or co-culture involving multiple cells types and multiple ECM coatings can be tested in a single 96-well plate. Assays can be performed using standard techniques which include the use of absorbance and fluorescence plate readers.

The various techniques, methods, and aspects of the invention described above can be implemented in part or in whole using computer-based systems and methods. Particularly, the regulation of spot size and location on a substrate can be regulated by a computer system operably connected to a spotting device (e.g., a DNA spotting device). Additionally, computer-based systems and methods can be used to augment or enhance the functionality described above, increase the speed at which the functions can be performed, and provide additional features and aspects as a part of or in addition to those described elsewhere in this document. Various computer-based systems, methods and implementations in accordance with the above-described technology are presented below.

A processor-based system can include a main memory, preferably random access memory (RAM), and can also include a secondary memory. The secondary memory can include, for example, a hard disk drive and/or a removable storage drive, representing a floppy disk drive, a magnetic tape drive, an optical disk drive, etc. The removable storage drive reads from and/or writes to a removable storage medium. Removable storage medium refers to a floppy disk, magnetic tape, optical disk, and the like, which is read by and written to by a removable storage drive. As will be appreciated, the removable storage medium can comprise computer software and/or data.

In alternative embodiments, the secondary memory may include other similar means for allowing computer programs or other instructions to be loaded into a computer system. Such means can include, for example, a removable storage unit and an interface. Examples of such can include a program cartridge and cartridge interface (such as the found in video game devices), a movable memory chip (such as an EPROM or PROM) and associated socket, and other removable storage units and interfaces, which allow software and data to be transferred from the removable storage unit to the computer system.

The computer system can also include a communications interface. Communications interfaces allow software and data to be transferred between computer system and external devices. Examples of communications interfaces can include a modem, a network interface (such as, for example, an Ethernet card), a communications port, a PCMCIA slot and card, and the like. Software and data transferred via a communications interface are in the form of signals, which can be electronic, electromagnetic, optical or other signals capable of being received by a communications interface (e.g., information from flow sensors in a microfluidic channel or sensors associated with a substrates X-Y location on a stage). These signals are provided to communications interface via a channel capable of carrying signals and can be implemented using a wireless medium, wire or cable, fiber optics or other communications medium. Some examples of a channel can include a phone line, a cellular phone link, an RF link, a network interface, and other communications channels. In this document, the terms "computer program medium" and "computer usable medium" are used to refer generally to media such as a removable storage device, a disk capable of installation in a disk drive, and signals on a channel. These computer program products are means for providing software or program instructions to a computer system. In particular, the disclosure includes instructions on a computer readable medium for calculating the proper $O_2$ concentrations to be delivered to a bioreactor system comprising particular dimensions and cell types.

Computer programs (also called computer control logic) are stored in main memory and/or secondary memory. Computer programs can also be received via a communications interface. Such computer programs, when executed, enable the computer system to perform the features of the disclosure including the regulation of the location, size and content of a microspot or microwell on a substrate.

In an embodiment where the elements are implemented using software, the software may be stored in, or transmitted via, a computer program product and loaded into a computer system using a removable storage drive, hard drive or communications interface. The control logic (software), when executed by the processor, causes the processor to perform the functions of the invention as described herein.

In another embodiment, the elements are implemented primarily in hardware using, for example, hardware components such as PALs, application specific integrated circuits (ASICs) or other hardware components. Implementation of a hardware state machine so as to perform the functions described herein will be apparent to person skilled in the relevant art(s). In yet another embodiment, elements are implanted using a combination of both hardware and software.

The methods and systems of the invention have been demonstrated as set forth in more detail in the Examples. The utility of this approach, for example, has been demonstrated by application to two different cell types: assessing the differentiated function of mature, primary rat hepatocytes by albumin immunostaining, and differentiation of murine embryonic stem (ES) cells along the hepatic lineage as assessed by a β-galactosidase reporter on an early liver-specific gene, Ankrd17 (gtar).

In one aspect, fabrication of a microarray for cell culture (e.g., an ECM microarray) was obtained by optimization of deposition methods, printing buffers, microarray surfaces, and cell culture conditions. In one aspect, a contact style arrayer using pins that deposit 1-2 nL, although larger amounts can be used, of material per ~150 μm (e.g., 90-200 μm) diameter spot—large enough to accommodate about 5-50 cells (e.g., about 20 cells)—can be used. In some instances (e.g., where ECM materials are used) a modified spotting buffer is used. The modified buffer comprises an acidic buffer to inhibit collagen polymerization, 5 mM EDTA (to prevent laminin polymerization), triton X-100 (to reduce surface tension), and glycerol (to slow evaporation and increase the volume of material deposited). In addition, cleaning and maintenance between fabrication steps or runs can be performed. For example, dipping the pins in dimethyl sulfoxide (DMSO) between wells, and routine (e.g., daily) sonication of the pins, can assist in reducing defects during consecutive printing runs.

The working examples provided below are to illustrate, not limit, the disclosure. Various parameters of the scientific methods employed in these examples are described in detail below and provide guidance for practicing the disclosure in general.

EXAMPLES

ECM Microarray Fabrication.

The microarray substrate was a custom fabricated acrylamide gel pad slide, similar to the Hydrogel slide (Perkin Elmer). To summarize, glass slides were modified with 3-(trimethoxysilyl)propyl methacrylate (Sigma) to present methacrylate groups which bond the gel to the glass. A thin (~80 μm) polyacrylamide gel pad was created by floating an untreated 22×22 mm #1 coverslip on a 40 μL drop of prepolymer solution, and exposing to UV at 1.5 mW/cm$^2$ for 10 minutes (Glo-Mark Systems, Inc.). The prepolymer solution consisted of 9.5% acrylamide, 0.5% bis, and 20 mg/mL 1-[4-(2-Hydroxyethoxy)-phenyl]-2-hydroxy-2-methyl-1-propane-1-one (Irgacure 2959, Ciba Specialty Chemicals; dissolved initially in methanol at 200 mg/mL). After carefully removing the coverslip, the slides were soaked in H$_2$O for 48 hours and dehydrated on a hotplate at 40° C. The printing buffer consisted of 100 mM acetate, 5 mM EDTA, 20% glycerol, 0.25% triton X-100 adjusted to pH=5.0 to inhibit protein polymerization. For ECM arrays, stock solutions of rat collagen I[8], human collagen III, mouse collagen IV, human fibronectin (Becton Dickinson), and mouse laminin (Sigma) were suspended at 500 μg/mL in the printing buffer. ECM protein solutions were then mixed in 32 combinations in a 384-well plate. Eight individual spots of each protein mixture were deposited with a 500 μm pitch on the acrylamide gel pad using a SpotArray 24 (Perkin Elmer) equipped with Stealth SMP 3.0 split pins (Telechem). The pins were cleaned by sonication in 5% Micro Cleaning Solution (Telechem) and H$_2$O immediately before use. Between each sample in the source plate, the pins were dipped in a 50% DMSO and water solution, washed for 25 seconds with H$_2$O, and dried. Twenty ECM microarrays could be produced simultaneously in this manner in one hour. A silicone well isolator (Grace Biolabs) was adhered around the gel pad using "Silicone II" sealant (General Electric) to define the cell culture area. The protein arrays with gaskets were incubated at 4° C. in a humidified environment for ~16 hours, and rinsed in PBS before use.

Cellular Function.

Images of the 9 mm×9 mm array were acquired at 10× as a series of 154 images on a Nikon inverted microscope equipped with a motorized stage (Ludl Electronic Products Ltd.). The images were montaged using Metamorph 6.2r3 software (Universal Imaging Corp.). Hepatocyte arrays were fixed on days 1 and 7 in 4% paraformaldehyde and stained for intracellular albumin using a rabbit anti-rat albumin antibody (Cappel) and a goat anti-rabbit IgG-Alexa 633 secondary (Molecular Probes). Arrays were mounted in Slowfade Light (Molecular Probes) and imaged using 3 second exposures for each frame (CoolSnap HQ, Photometrics).

I114 ES cell reporter expression was assessed at days 3 and 5. Cell arrays were fixed for 20 minutes in 0.5% glutaraldehyde and stained in 0.1% X-gal in a Tris buffer (pH 7.5) overnight at 37° C. Montaged images of each array were acquired in bright field. β-galactosidase image area was quantified by color thresholding using Metamorph software.

Indirect Immunofluoresence.

Five identically fabricated ECM microarrays were blocked using a 10% goat serum, 1% BSA solution in PBS. Indirect immunofluorescence was conducted using the following primary antibodies (all raised in rabbits), and an Alexafluor 633 goat anti-rabbit secondary (1:50 dilution, Molecular Probes): anti-rat collagen I (Chemicon), anti-mouse laminin (Chemicon), anti-human collagen III (Biodesign), anti-mouse collagen IV (Biodesign), and anti-human fibronectin (Sigma). Fluorescent images were acquired using a ScanArray 4000 confocal laser scanner (GSI Lumonics).

Cell Culture.

ECM microarray slides with silicone gaskets were placed in sterile P-100 culture dishes. The gasket area was filled with 300 μL of H$_2$O. Protein arrays were sterilized by exposure to UV in a laminar flow hood for 15 minutes, followed by rinsing in sterile culture media. ECM microarray slides with silicone gaskets were placed in sterile P-100 culture dishes. Hepatocytes were isolated from 2- to 3-month-old adult female Lewis rats (Charles River Laboratories, Wilmington, Mass.) weighing 180-200 grams, by a modified procedure of Seglen. Detailed procedures for isolation and purification of hepatocytes were described by Dunn et al. Routinely, 200-300 million cells were isolated with viability between 85 and 95%, as judged by trypan blue exclusion. Nonparenchymal cells, as judged by their size (<10 μm in diameter) and morphology (nonpolygonal or stellate), were less than 1%. Culture medium was Dulbecco's modified Eagle's medium (DMEM, Gibco) supplemented with 10% fetal bovine serum (FBS, Sigma, St. Louis, Mo.), 0.5 U/mL insulin, 7 ng/mL glucagon, 20 ng/ml. epidermal growth factor, 7.5 g/mL hydrocortisone, 100 U/mL penicillin, and 100 g/mL streptomycin. Hepatocytes were suspended at $10^6$ cells/mL in culture media. The cell suspension was dispensed onto the ECM microarray in the gasket region (0.3 mL), and incubated for ~2 hours to allow for cell attachment (shaking the plates every 15 minutes to redistribute the cells). The arrays were then gently aspirated to remove unattached cells and fresh culture media was added to the silicone wells. Culture media was changed daily. The I114 mouse embryonic stem cell line containing a gene-trap was propagated in an undifferentiated state on gelatinized flasks in culture media containing 1000 U/mL leukemia inhibitory factor (LIF, Chemicon). FS media consisted of GMEM/BHK21 (Gibco) supplemented with 15% FBS (Hyclone, screened for ES culture), non-essential amino acids, and $10^{-4}$ M 2-mercaptoethanol (Sigma). Cells were passaged at ~80% confluence (approximately every two days). ECM microarrays containing 450,000 cells were cultured for 6-10 hours (without shaking) to allow for cell attachment before rinsing with fresh media. ES cell arrays were cultured for up to six days with either 1000 U/mL LIF or $10^{-6}$ M all-trans-retinoic acid (Sigma).

Cellular Function.

Hepatocyte cell viability was assessed on day 1 and day 5 after plating using a live/dead assay (Calcein AM and ethidium homodimer-1, Molecular Probes Inc). Cell arrays were imaged live, and then fixed in 4% paraformaldehyde and mounted in SlowFade Light w/DAPI (Molecular Probes Inc.) for high resolution microscopy. I114 ES cell alkaline phosphatase activity was assessed by a substrate kit IV (SK-5400 Vector Laboratories). F-Actin was visualized using Phalloidin-TRITC (Sigma). Confocal volume images were acquired at 20× and 40× on a BioRad MRC 1000, and digitally sectioned in the x-z plane using Metamorph 6.2r3 software (Universal Imaging Corp.).

Statistics and Data Analysis.

Unless otherwise specified, all data are reported as average value±standard deviation. We assessed intracellular albumin content of hepatocytes using Metamorph image analysis software. To quantify spot intensity, we calculated the average pixel value within a masked region (each ECM microarray contained 256 spots). After a log transformation, the data appeared to be normally distributed with approximately equal variance. For each matrix mixture, the eight replicate log spot intensities were used to calculate the average signal and standard error for the condition. Two day 1-, and four day 7-arrays were quantified in this manner. The mean signal for each array was adjusted to an arbitrary common value among arrays. All normalized day 7 data were analyzed as a 25 full factorial design with 4 blocks (one for each microarray) using Minitab statistical software (Minitab, State College, Pa.). Main effects, 2-factor, 3-factor, and 4-factor interactions, along with the statistical significance of each of these properties, were calculated using standard factorial analysis formulae. The residuals were normally distributed with approximately equal variance around a mean value of zero. β-galactosidase analysis of ES cultures was performed similarly using data from 4 day-3 arrays.

ECM Microarray Fabrication and Characterization.

Figure 9:
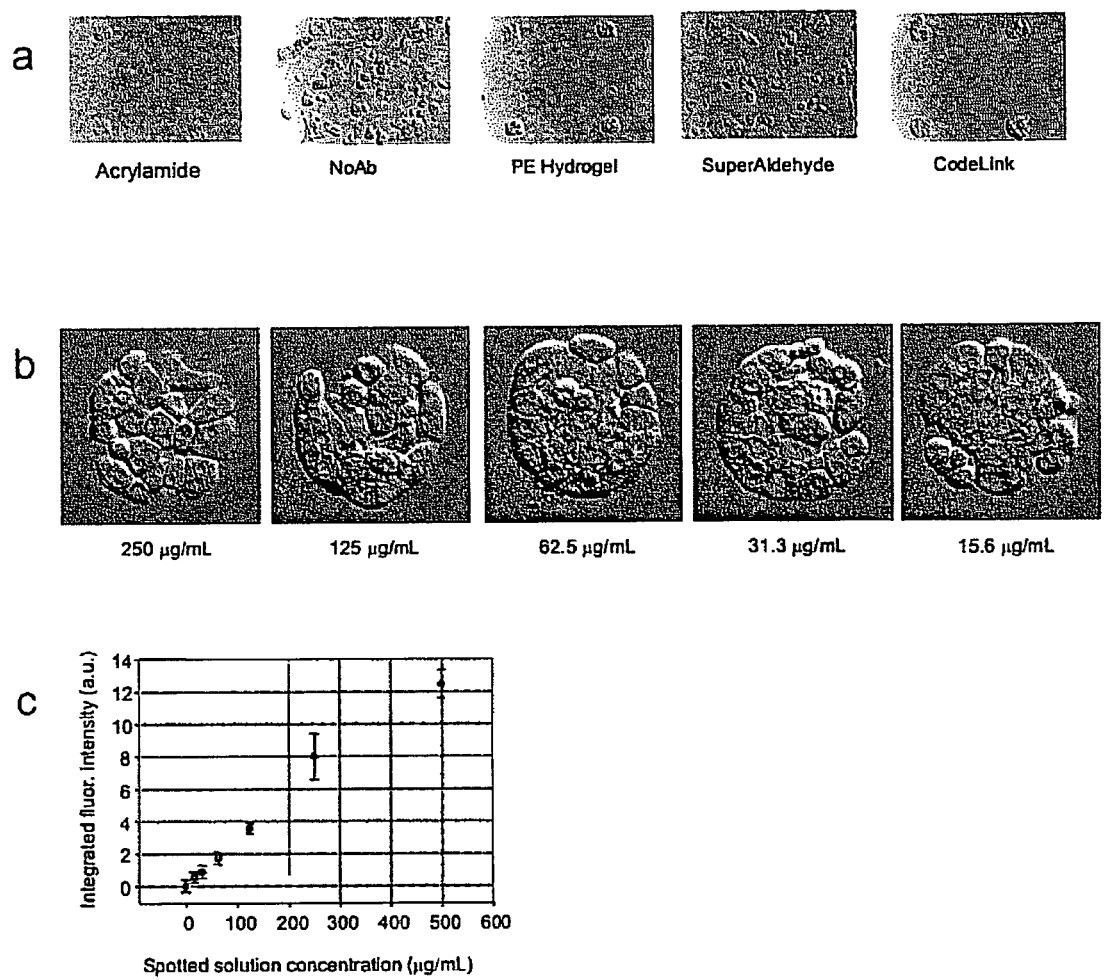
FIG. 9A-C show photomicrographs of hepatocyte cultures. (A) Primary hepatocytes attach to collagen I spots, and are spatially confined on the custom acrylamide, CodeLink (Amersham), and Hydrogel (Perkin Elmer) substrates. Superaldehyde (Telchem) and Epoxy Hydrogel (NoAb Diagnostics) allow cell attachment in non-spotted regions. (B) Primary hepatocytes attached to collagen I spots made from solutions containing as little as 15.6 µg/mL of protein. Below this concentration non cell attachment was observed. Hepatocytes showed similar attachment to serially diluted collagen III, collagen IV, Laminin, and fibronectin. (C) Immobilized FITC-collagen I signal is linear over a broad range of spotting solution protein concentrations. Error bars represent S.E.M.

Some of the design criteria were: 1) minimal protein usage; 2) reproducible fabrication; 3) low protein carryover; 4) nonadhesive microarray surface for cells; 5) compatibility with diverse cell types; 6) maintain cell patterns for ~1 week in serum media; and 7) compatible with conventional microscopy. A contact deposition type microarrayer over a piezo dispenser fit these criteria because it can function with as little as 3 μL of source material. Several commercially microarray surfaces were tested for their ability to confine hepatocytes to collagen I islands (a model ECM protein) for 48 hours of culture with 10% serum. Hydrogel (Perkin Elmer), CodeLink (Amersham), and acrylamide slides maintained spatially confined cellular islands for ~48 hours (FIG. 9A-C). A wide range of spotting solution concentrations were permissive for cell attachment.

Protein immobilization was verified and assessed to determine whether substantial carryover occurred during the fabrication process. Spatial localization of ECM proteins was determined using antigenic recognition. In each case, a high level of fluorescence corresponded to the expected spatial distribution of the five matrix proteins used. Collagen IV staining showed dim fluorescence in some laminin regions, likely corresponding to a reported 4% cross reactivity of the antibody as assessed by radio-immunoassay (Biodesign International). Alternating test solutions of FITC-collagen I and "buffer only" were also spotted with the same pin. No signal was detected in "buffer only" rows using a confocal laser scanner. Thus no protein carryover contamination was detected using two separate techniques.

Primary rat hepatocytes adhered to protein spotted regions, and did not attach to the acrylamide gel regions lacking ECM proteins. The cell patterning was robust over a large surface area (9 mm×9 mm), yielding a uniform array of near confluent cellular islands with a diameter of 150 μm±5.8 μm (N=15). Cells were confined to the spotted regions for a period of at least 7 days, after which the most common mode of failure was gel detachment from the slide. Phase contrast images of the array showed compact cells with polygonal morphology, distinct nuclei, and bright intercellular borders consistent with primary hepatocytes. The cell viability (assayed with Calcein Am/Ethidium homodimer-1) at 24 hours and 5 days after plating showed predominantly live cells (~95%) with intact membranes that excluded ethidium homodimer-1 nuclear staining.

Effect of ECM Composition on Hepatocytes and ES Cells.

Figure 7:
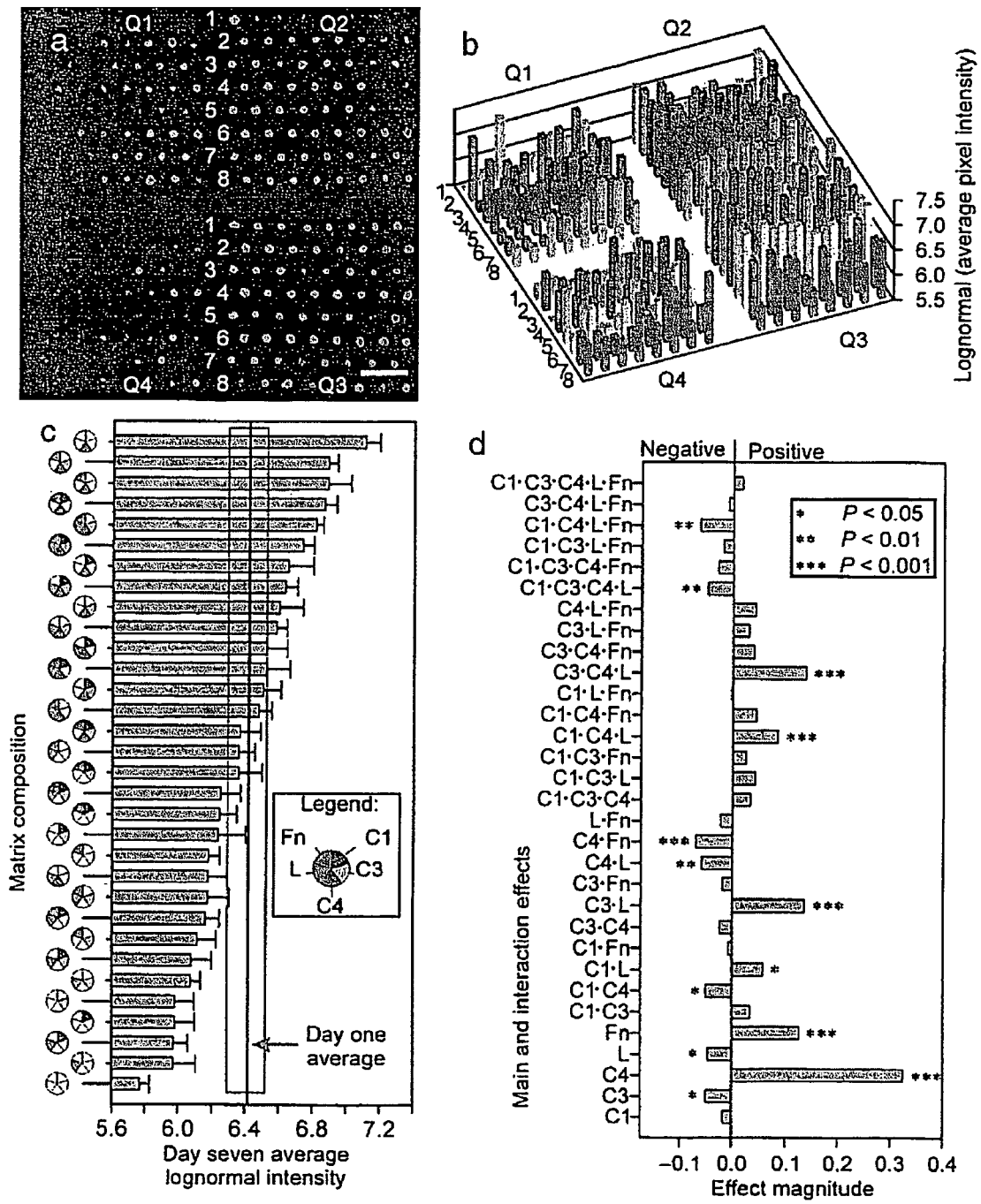
FIG. 7A-D shows cultured hepatocytes demonstrate differential intracellular albumin staining in response to matrix composition. (A) Indirect immunofluorescence of intracellular albumin, a marker of differentiated hepatocyte function, on day 7. Note preservation of microarray features after 7 days in 10% serum. (B) Quantitation of average pixel intensity per microarray spot in panel A. (C) Hierarchical depiction of image albumin intensity for each of the matrix mixtures on day 7. Error bars represent s.e.m. (N=8). Reference line is the average intensity for hepatocytes on day 1. Error box represents 1 s.d. (D) Results of 25 full factorial analysis on intracellular albumin intensity (4 microarray data sets). The relative magnitude of main effects as well as 2-, 3-, 4-, and 5-factor interactions are shown. Q1, quadrant 1; Q2, quadrant 2; Q3, quadrant 3; Q4, quadrant 4; C1, collagen I; C3, collagen III; C4, collagen IV; L, laminin; Fn, fibronectin.

In order to probe primary rat hepatocytes for the effects of ECM composition, cell arrays were stained immunofluorescently for intracellular albumin (a marker of liver-specific function) and analyzed at days 1 and 7. All islands exhibited similar fluorescent intensity on day 1, with an average of 6.41 log fluorescent units±0.166 (two arrays measured). In contrast, day 7 arrays showed notable differences in fluorescent intensity that appeared to be dependent on the initial underlying matrix composition. Quadrants 2 and 3 of the array have collagen IV in all spots, and appeared qualitatively and quantitatively to be brighter than quadrants 1 and 4 (FIG. 7A-B). Approximately half of the analyzed mixtures had an albumin signal on day 7 that was greater than the average of day 1 cultures (FIG. 7C). Of note, the 15 highest albumin signals are associated with underlying matrices containing collagen IV. In a separate experiment, hepatocytes cultured on serially diluted collagen IV (ranging from 31.2 μg/mL to 500 μg/mL) for five days showed no significant differences in intracellular albumin signal (P=0.05 for all pairs using one-way ANOVA with a multiple comparison Tukey post-hoc test, GraphPad Prizm). Taken together, the data suggested that the differences in liver-specific function were not simply due to a difference in collagen IV concentration but rather an interactive effect with other ECM molecules.

Factorial analysis methods were applied to analyze all available day 7 data (4 arrays=1024 data points) for main effects, 2-, 3-, and 4-factor interactions, in addition to the statistical significance of each effect (FIG. 7D). The analysis revealed that collagen IV had the largest overall effect on albumin signal. Among the other main effects, fibronectin also had a positive effect, though to a lesser extent than collagen IV. Laminin and collagen III were found to negatively impact albumin signal. In agreement with these findings, it has been previously reported that secreted albumin from primary rat hepatocytes is highest when cultured on collagen IV, and decreases when cultured on fibronectin and laminin respectively. Interestingly, a number of 2-, 3-, and 4-factor interactions were also identified as statistically significant (P=0.05). The interaction of collagen I with laminin, and collagen III with laminin both had positive effects. However, each of these components individually exhibited a negative effect, suggesting a non-additive interaction. Similarly, the interaction of collagen IV with fibronectin showed a negative effect, whereas individually these components displayed positive effects.

Figure 8:
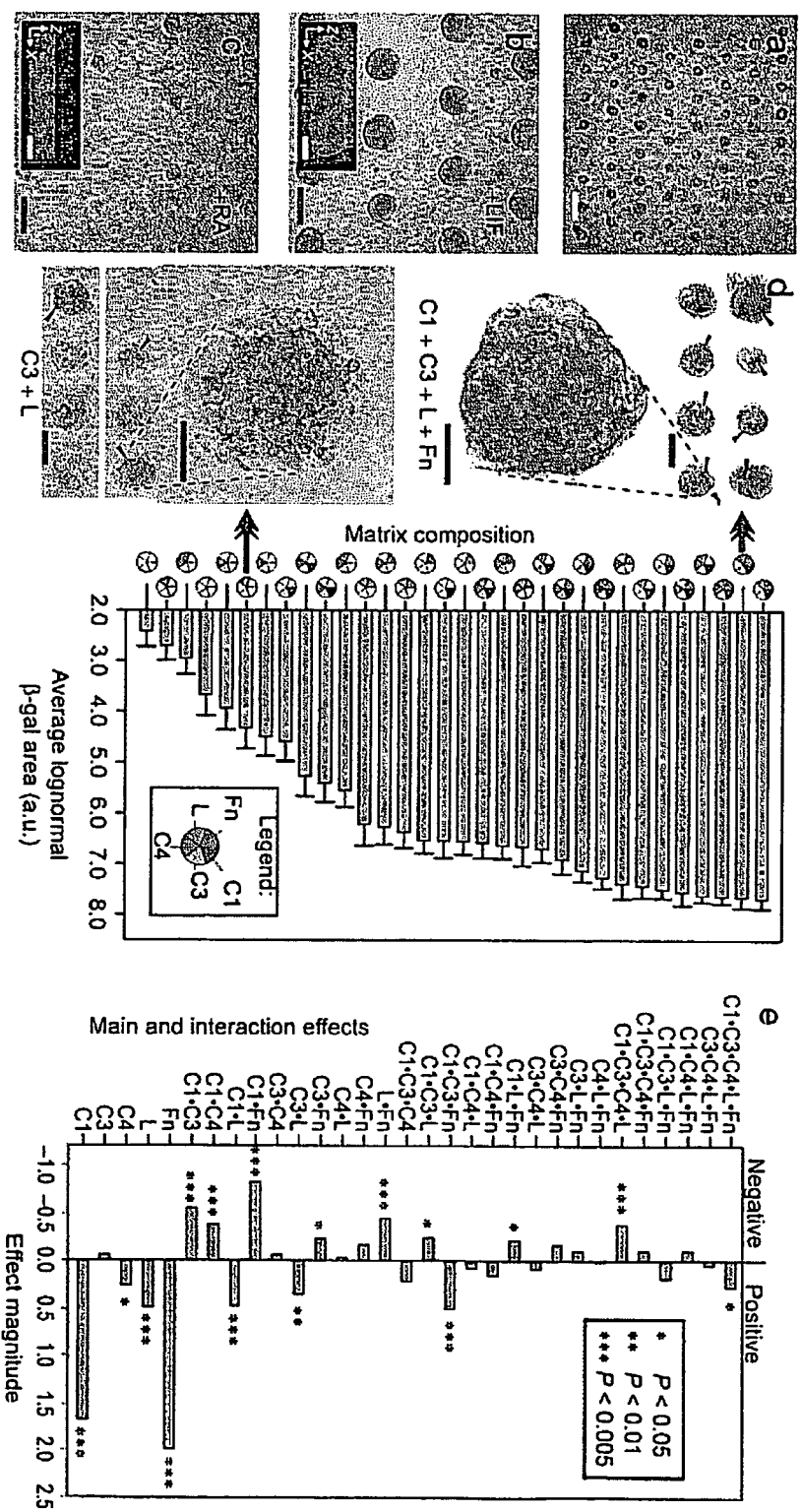
FIG. 8A-E demonstrates that I114 embryonic stem cells differentiate on ECM microarrays. (A) Bright field alkaline phosphatase staining of day 1 ES cultures on ECM microarrays in 15% serum media (scale bar, 1 mm). (B) Phase contrast images of day 3 arrays cultured with LIF, and with RA (C). Cells cultured with LIF showed 3-dimensional features (see (B) inset x-z confocal section, ~77 µm thickness). In contrast, RA-induced cells grew as a relatively thin sheet (see (C) and inset x-z section, ~25 µm thickness). Scale bars, 250 µm (inset scale bars, 50 µm). (D) (top left images) Bright field micrograph of selected X-gal stained ECM microarray conditions after 3 days of culture in RA. C1+C3+L+Fn induced higher levels of Ankrd17 (gtar) reporter activity (arrowheads) than cells cultured on C3+L (bottom left images). Scale bars, 250 µm. Magnified views of reporter activity: scale bars, 50 µm. Bar graph: hierarchical depiction of "blue" image area (pooled data from 4 microarrays) for each of the matrix mixtures. Error bars represent s.e.m. (N=32). The C1+C3+L+Fn culture condition induced ~27-fold more β-galactosidase image area than the C3+L cultures. (E) Results of 25 full factorial analysis on β-galactosidase positive "blue" image area (4 microarray data sets). The relative magnitude of main effects as well as 2-, 3-, 4-, and 5-factor interactions are shown. C1, collagen I; C3, collagen III; C4, collagen IV; L, laminin; Fn, fibronectin.

To investigate the feasibility of using matrix arrays to study stem cell differentiation, murine embryonic stem 1114 cells were cultured for up to 6 days in the presence of 1000 U/mL leukemia inhibitory factor (LIF) or $10^{-6}$ M all-trans-retinoic acid (RA). Day 1 cultures stained uniformly positive for alkaline phosphatase (FIG. 8A). Cells cultured with LIF for three days (FIG. 8B) grew as 3-dimensional clusters that were reminiscent of embryoid bodies (EB's) with an average diameter 224 μm±12 μm (N=14). Confocal sectioning (FIG. 8B inset) indicated that islands were ~77 μm in thickness (likely multi-layered). When cultured with RA, the cells grew as a relatively thin sheet of thickness ~25 μm (FIG. 8C inset). Notably, several matrix conditions in day 3 and 5 RA-induced cultures elicited a substantial increase of β-galactosidase reporter activity when stained with X-gal. For example, collagen I+collagen III+laminin+fibronectin collectively induced noticeably more reporter expression in all replicate islands (FIG. 8D, top left images) than cells cultured on collagen III+laminin (FIG. 8D, bottom left images). Quantitative image analysis of "blue" thresholded area in day 3 RA-treated arrays illuminated further trends (FIG. 8D, bar graph). Nine of the 10 highest signals were recorded from cells on matrices that contained collagen I, and 4 of the top 5 signals came from ECM conditions with both collagen I and fibronectin. The lowest 11 signals were detected on matrices that lacked fibronectin, and matrices which lacked both collagen I and fibronectin produced the lowest 7 β-galactosidase signals. A 25 full factorial analysis on data from 4 arrays also indicated that fibronectin and collagen I had strong positive effects on β-galactosidase reporter expression (FIG. 8E). Again, a number of potentially counter-intuitive interaction effects were identified (e.g. collagen I+collagen IV, and collagen I+fibronectin).

Although a number of embodiments and features have been described above, it will be understood by those skilled in the art that modifications and variations of the described embodiments and features may be made without departing from the teachings of the disclosure or the scope of the invention as defined by the appended claims.

What is claimed is:

1. A cell culture system, comprising:
   (a) a cell culture substrate;
   (b) a hydrogel layered on said cell culture substrate, wherein said hydrogel is non-adhesive for cells, wherein said hydrogel is dehydrated after being layered, and
   wherein at a plurality of discrete locations on hydrogel is deposited from about 1 to about 1000 nanoliters of one or a mixture of cell adherence materials, or a combination of one or a mixture of cell adherence materials and one or a mixture of soluble factors to form a microarray, wherein the cell adherence material is a biomolecule that promotes cellular adhesion, wherein said biomolecule is selected from the group consisting of proteins, peptides, oligonucleotides, polynucleotides, polysaccharide, proteoglycans, glycoproteins, glycosaminoglycans, and lipids; and
   (c) one or more cell types adhered to one or more locations of the microarray so as to form a micropattern of spatially separated cellular islands,
   wherein the micropattern is capable of being maintained for up to 7 days in cell culture.

2. The cell culture system of claim 1, wherein the hydrogel is dehydrated polyacrylamide hydrogel.

3. The cell culture system of claim 1, wherein the biomolecule is a protein.

4. The cell culture system of claim 3, wherein the protein is an extracellular matrix protein.

5. The cell culture system of claim 1, wherein at a plurality of microarray locations is spotted one or a mixture of cell adherence materials and one or a mixture of soluble factors.

6. The cell culture system of claim 1, wherein the discrete locations in the microarray are microwells.

7. The cell culture system of claim 1, wherein the discrete locations in the microarray are microspot islands.

8. The cell culture system of claim 1, further comprising a plurality of microfluidic channels connecting one or more of the discrete locations in the microarray to a fluid flow.

9. The cell culture system of claim 1, wherein the mixture of adherence materials at each microarray location is different.

10. The cell culture system of claim 1, wherein the mixture of adherence materials at each microarray location is the same.

11. The cell culture system of claim 1, wherein the one or more cell types adhered to the plurality of microarray locations are different at each of the plurality of array locations.

12. The cell culture system of claim 1, wherein the one or more cell types adhered to the plurality of array locations are the same at each of the plurality of array locations.

13. A method of making a cell culture microarray, comprising:
   (a) obtaining a cell culture substrate;
   (b) layering onto said cell culture substrate a hydrogel, wherein said hydrogel is non-adhesive for cells;
   (c) dehydrating said hydrogel layered on said cell culture substrate;
   (d) spotting at a plurality of discrete locations on said dehydrated hydrogel from about 1 to about 1000 nanoliters of one or a mixture of cell adherence materials, or a combination of one or a mixture of cell adherence materials and one or a mixture of soluble factors to form a microarray, wherein the cell adherence material is a biomolecule that promotes cellular adhesion, wherein said biomolecule is selected from the group consisting of proteins, peptides, oligonucleotides, polynucleotides, polysaccharides, glycoproteins, proteoglycans, glycosaminoglycans, and lipids; and
   (e) adhering one or more cell types to one or more locations comprising cell adherence materials so as to form a micropattern of spatially separated cellular islands, wherein the micropattern is capable of being maintained for up to 7 days in cell culture.

14. The method of claim 13, wherein the cell adherence material is a protein.

15. The method of claim 14, wherein the protein is an extracellular matrix protein.

16. The method of claim 13, wherein the dehydrated hydrogel layered on the cell culture substrate is etched at each of the plurality of locations to form microwells.

17. The method of claim 13, further comprising incorporating fluid flow channels fluidly connecting each location with a fluid flow.

18. The method of claim 13, wherein the one or more cell types comprise two or more cell types.

19. The method of claim 18, wherein the two or more cell types comprise of stromal cells and parenchymal cells in coculture.

20. The method of claim 13, wherein the one or more cell types comprise parenchymal cells.

21. The method of claim 20, wherein the parenchymal cell is a hepatocyte.

22. The method of claim 13, wherein the hydrogel is a polyacrylamide hydrogel.

23. The method of claim 13, wherein the spotting is performed by a spotting device.

24. The method of claim 23, wherein the device is a DNA spotting device.

25. The method of claim 13 or 24, wherein each of the plurality of locations comprise the same adherence material.

26. The method of claim 13 or 24, wherein at least two of the plurality of locations comprise different adherence materials.

27. The method of claim 23, wherein the cell adherence materials are spotted in a printing buffer.

28. The method of claim 27, wherein the printing buffer comprises 100 mM acetate, 4 mM EDTA, 20% glycerol and 0.25% Triton X-100 at pH 5.0.

* * * * *